United States Patent [19]

He et al.

[11] Patent Number: 5,679,566
[45] Date of Patent: Oct. 21, 1997

[54] YEAST NMD2 GENE

[75] Inventors: Feng He, Worcester; Allan S. Jacobson, Grafton, both of Mass.

[73] Assignee: University of Massachusetts Medical Center, Worcester, Mass.

[21] Appl. No.: 375,300

[22] Filed: Jan. 20, 1995

[51] Int. Cl.$^6$ .............................. C12N 1/19; C12N 1/21; C12N 15/63; C12N 15/85

[52] U.S. Cl. ............... 435/240.2; 435/69.9; 435/172.3; 435/240.1; 435/252.3; 435/254.2; 536/23.1; 536/23.7

[58] Field of Search .............................. 536/23.1, 23.7; 435/320.1, 240.1, 240.2, 252.3, 254.2, 69.9, 172.3

[56] References Cited

PUBLICATIONS

Johnston et al. Complete Nucleotide Sequence of *Saccharomyces cerevisiae* Chromosome VIII. Science, 265:2077–1082. 1994.

Johnston et al., The complete sequence of *Saccharomyces cerevisiae* chromosome VIII, Genebank, Accession No. U10556. 1994.

Sambrook et al., Molecular Cloning: A Laboratory Mannual, Cold Spring Harbor Laboratory Press, p. 3.18. 1989.

Stuart W. Peltz et al., "Nonsense–mediated mRNA decay in yeast," *Prog. Nucl. Acids Res. and Mol. Biol.* 47:271–297 (1994).

Feng He et al., "Stabilization and ribosome association of unspliced pre–mRNAs in a yeast upf1 mutant," *Proc. Natl. Acad. Sci. USA*, Biochemistry, 90:7034–7038 (1993).

Stuart W. Peltz et al., "mRNA destabilization triggered by premature translational termination depends on at least three cis–acting sequence elements and one trans–acting factor," *Genes & Development*, Cold Spring Harbor Laboratory Press, 7:1737–1754 (1993).

Peter Leeds et al., "Gene products that promote mRNA turnover in *Saccharomyces cerevisiae*," *Molecular and Cellular Biology* 12(5):2165–2177 (1992).

Nicola Altamura et al., "NAM7 nuclear gene encodes a novel member of a family of helicases with Zn–ligand motif and is involved in mitochondrial functions in *Saccharomyces cerevisiae*," *J. Mol. Biol.* 224:575–587 (1992).

Stanley Fields et al., "A novel genetic system to detect protein–protein interactions," *Nature* 340:245–246 (1989).

Jun Ma et al., "Converting a eukaryotic transcriptional inhibitor into an activator," *Cell* 55:443–446 (1988).

*Primary Examiner*—John L. LeGuyader
*Assistant Examiner*—Thanda Wai
*Attorney, Agent, or Firm*—Fish & Richardson P.C.

[57] ABSTRACT

The invention relates to the discovery of a gene, NMD2, named after its role in the Nonsense-Mediated mRNA Decay pathway, and the protein, Nmd2p, encoded by the NMD2 gene. The amino acid sequence of Nmd2p and the nucleotide sequence of the NMD2 gene encoding it are disclosed. Nmd2p is shown herein to bind to another protein in the decay pathway, Upf1p. A C-terminal fragment of the protein is also shown to bind Upf1p and, when overexpressed in the host cell, the fragment inhibits the function of Upf1p, thereby inhibiting the nonsense-mediated mRNA decay pathway. The invention also relates to methods of inhibiting the nonsense-mediated mRNA decay pathway to stabilize mRNA transcripts containing a nonsense codon which normally would cause an increase in the transcript decay rate. Such stabilization of a transcript is useful for the production of a recombinant protein or fragment thereof.

14 Claims, 6 Drawing Sheets
(1 of 6 Drawing(s) in Color)

```
2280 GATAATTATTCAGGATTCAACTAGTCACTGACAATTCTGTAAAATATCAACGGACCCCTGAGCTTTACTAAGAAATGCAACTTTGCTGAGTTTTGAGTATATACTTTTATT
 723  D  N  Y  F  R  I  Q  L  V  T  T  I  L  L  N  I  N  R  T  P  A  A  F  T  K  K  C  K  L  L  R  F  F  E  Y  Y  T  F  I
2400 AAGAGAACCCTTGACCCAGGAAACAGAATTCAGTTTCAAGACATTAAAAATATAGAAATATTTCAAAAATGCTAAATTGAAGCTAAATTTGTTAGAAGTGCCTCA
 763  K  E  Q  P  L  P  K  E  T  E  F  R  V  S  S  T  F  K  K  Y  E  N  I  F  G  N  T  K  F  E  R  S  E  N  L  V  E  S  A  S
2520 AGTTGGAAAGTTTACTGAAATCATTGAAAGTAAAAGTACAACACAGATGAAGGATCTTCTGCAAGCGTAAGAGTCTGTCCATCAGTCATTCACC
 803  R  L  E  S  L  L  K  S  L  N  A  I  K  S  K  D  D  R  V  K  G  S  S  A  S  I  H  N  G  K  E  S  A  V  P  I  E  S  I  T
2640 GAAGACGAAAGTGAAGATGAAGATGAAAACGACGATGCATTACTAGGAGAAGATGAAGACGCCGGACAGAGTACACCGAACACAGAGTCACCGCCGAAAACATCAGGCAAAG
 843  E  D  D  E  D  E  D  D  E  N  D  D  G  V  D  L  L  G  E  D  E  A  E  I  S  T  P  N  T  E  S  A  P  G  K  H  Q  A  K
2760 CAAGACGAAAGTGAAGATGAAGACGATGATGAAGACGATGAGGACGATGATGAAGAAGAAGACGATGATGATGAAGAAGGGATGATGAAGATGATGATGAGGATGAAGATGAT
 883  Q  D  E  S  E  D  E  D  D  D  E  D  D  E  D  D  D  D  D  D  D  G  E  E  G  D  E  D  D  D  D  D
2880 GAGGATGATGATGAAGAAGAAGACAGCGACTCTGATTTGAAGTATGGTGATCTAGAGTATCTTGACGCAGAAGAATGATGAAGATATTGAAATGAAACGAATGTATGAAGTATGCAGTAATTCCAGTATAATTGTTATT
 923  E  D  D  D  D  E  E  E  E  D  S  D  L  E  Y  G  G  D  L  D  A  D  R  D  I  E  M  K  R  M  Y  E  E  Y  E  R  K  L
3000 AAGGATGAAGAAGAAAGGAAAGCGGAAGAAGAATTGAAAAGACAATTCAGAAAGATGATCAAGAATCATAGAGCCAAGAAAATCCATAGACGAAGCAGCTAAAATTCCAGTAGTTATT
 963  K  D  E  E  E  R  K  A  E  E  E  L  E  R  Q  F  Q  K  M  M  Q  E  S  I  D  A  R  K  S  E  K  V  V  A  S  K  I  P  V  I
3120 TCGAAGCCAGTCAGCGTTCAGGTCCAAAACCTTATTATTAAAAAGAGTGAGGAACCTCTTCCAAGCAAGAGTTATCCAACCAAGAATTGCATTGCATTGCATTTACTTCTTTGACT
1003  S  K  P  V  S  V  Q  K  P  L  L  L  K  K  S  E  E  P  S  S  S  K  E  T  Y  E  E  L  S  K  P  K  K  I  A  F  T  F  L  T
3240 AAAAGCGGTAAGAAGACAACAGACATCAAGAATTTACAATTACAACGGATGTGAACTTGAAGAGAAGAACGAGCGAAACTAAAACCGAGCGAAAACTAAAACCGAGAAATTAAAGATT
1043  K  S  G  K  K  T  Q  S  R  I  L  Q  L  P  T  D  V  K  F  V  S  D  V  L  E  E  E  K  L  K  T  E  R  N  I  K  K  I
3360 GTTTTAAACGTTCTTTCGACTGAGATTCTTTGCCGAATTATAGTTCTTTAAATTTTACTATATGTTTGGCTCTATTATATGCCTACGTTGTTTATATATATAGATACCGTTAT
1083  V  L  K  R  S  F  D  *                        SEQ ID NO: 2 (aa 1-1089) SEQ ID NO: 4 (aa 326-1089) SEQ ID NO: 3 (nt 1089-3383)
3480 GACGCTGTATTTTATTTTACACTGCTTTCCAGGAGATTAAAGACGCGAGTGTAGTAGAATTTATTCAACTCTCACGAACAACAGTTTATATCGTCTCTTCTTTACCACCGCTGTAGTTTTTGCCAGTAG
3600 CTTAGAAATCTCTTGCCGAAAAACACTGGGGTCCTTGCCTTAAACTGACAACATTGTCCACAAACTTCTGGATAATAGCCTGTAACTCATCGTTTGTTCTCGCAGGTTATC
                                                                                                                                SEQ ID NO: 1
```

FIG. 2C

YEAST NMD2 GENE

STATEMENT AS TO FEDERALLY SPONSORED RESEARCH

This invention was made at least in part with funds from the Federal government, and the government therefore has rights in the invention.

BACKGROUND OF THE INVENTION

It is well known in the field of biology that changes in the amino acid sequence of a protein can result in changes in the biological function of the protein. To optimize a target biological function, the amino acid sequence can be altered and tested for improved function. In very simple terms, this is the process of evolution by which the proteins that exist naturally today have been selected over eons. It is an advantage of modern molecular biology that such alterations can be made in a matter of days rather than a matter of centuries. Specifically, optimizing the biological function of a protein of pharmaceutical or other commercial interest can be performed by substituting one amino acid for the naturally occurring amino acid at a given site and producing a sufficient quantity of the protein for screening of biological activity.

Production of a recombinant protein in a cellular system requires the efficient translation of the mRNA transcript encoding the protein. For this to occur, the transcript must exist in the cell long enough for translation into the desired recombinant protein. mRNA transcripts vary in the length of time (transcript half-life) that they exist in a cell prior to being degraded by cellular proteins specific for that purpose. In some cases, degradation occurs rapidly such that very little protein is produced.

For example, the yeast cell, *Saccharomyces cerevisiae*, a commonly used cellular system for the production of recombinant proteins, has a biological pathway that specifically degrades mRNA transcripts containing a non-coding triplet sequence (nonsense or stop codons) in the transcript. In several genes studied thus far, the destabilizing nonsense codon occurs within the 5'-proximal portion of the transcript (reviewed in Peltz et al., Prog. Nucl. Acids Res. and Mol. Biol. (1994) 47:271–297). The translation process stops at the nonsense codons prior to reaching the end of the transcript's coding sequence resulting in the production of a truncated protein that may not possess normal biological activity. Thus, the cell has developed a biochemical system to degrade transcripts containing mutations that create stop codons early in the coding sequence.

However, in a cell of a suppressor strain that suppresses nonsense codons, a nonsense codon can be a useful means of coding for an alternate amino acid when a nonsense codon is engineered into the coding sequence to produce an altered protein which is then screened for enhanced biological activity. Suppressor strains (e.g., SUF1-1) do not allow maximal expression of a nonsense codon-containing transcript (Leeds et al., (1991) Genes & Development 5:2303–2314).

Nonsense-mediated mRNA decay is a phenomenon in which nonsense mutations, e.g., point or frame shift mutations that create a stop codon in the reading frame, in a gene can enhance the decay rate of the mRNA transcribed from that gene. For a review, see, e.g., Peltz et al., (1994) Prog. Nucleic Acid Res. Mol. Biol. 47:271–297. The process occurs in viruses, prokaryotes, and eukaryotes (Leeds (1991), supra; Barker, G. F. and Beemon, K. (1991) Mol. Cell Biol. 11:2760–2768; Lim, S.-K. and Maquat, L. E. (1992) EMBO J 11:3271–3278).

In most genetic systems, 61 of the 64 possible codon triplets encode amino acids. The triplets UAA, UAG, and UGA are non-coding (nonsense codons) and promote translational termination (Osawa et al., (1992) Microbiol. Rev. 56:229–264). The polypeptide chain terminating effects of UAA, UAG, and UGA triplets have been amply documented and characterized (Craigen et al., (1990) Mol. Microbiol. 4:861–865).

Nonsense-mediated mRNA decay has been studied extensively in the yeast *Saccharomyces cerevisiae* where it has been shown that degradation of mRNA via this pathway is most likely to occur in the cytoplasm and is linked to translation. Evidence in support of these conclusions includes the following: 1) unstable, nonsense-containing mRNAs are stabilized in a strain harboring an amber suppressor tRNA (Losson and Lecroute, (1979) Proc. Natl. Acad. Sci. 76:5134–5137; Gozalbo and Hohmann, (1990) Curr. Genet. 17:77–79); 2) nonsense-containing mRNAs are ribosome-associated (Leeds et al., (1991) Genes & Devel 5:2303–2314; He et al., (1993) Proc. Natl. Acad. Sci. 90:7034–7039) and the number of ribosomes associated with such mRNAs is a function of the relative positions of the respective nonsense codons (He et al., (1993) Proc. Natl. Acad. Sci. 90:7034–7039); and 3) treatment of cells with cycloheximide, an inhibitor of translational elongation, stabilizes nonsense-containing mRNAs, yet removal of cycloheximide leads to the immediate restoration of rapid mRNA decay (Peltz et al., (1993) Genes & Devel 7:1737–1754).

Previous studies of nonsense-mediated mRNA decay in yeast also have shown that the products of the UPF1 and UPF3 genes (proteins Upf1p and Upf3p, respectively) are essential components of this degradative pathway. Mutations in these genes stabilize mRNAs containing premature nonsense codons without affecting the decay rates of most wild-type transcripts (Leeds et al., (1991) Genes & Devel 5:2303–2314, Leeds et al., (1992) Mol. Cell. Biol. 12:2165–2177; Peltz et al., (1993) Genes & Devel 7:1737–1754He et al., (1993) Proc. Natl. Acad. Sci. 90:7034:7039).

The UPF1 gene has been cloned and sequenced, (Leeds, P. et al., (1992) Mol. Cell Biol. 12:2165–2177) and shown to be: 1) non-essential for viability; 2) capable of encoding a 109 kD protein with a so-called zinc finger, nucleotide (GTP) binding site, and RNA helicase motifs (Leeds et al., (1992) Mol. Cell. Biol. 12:2165–2177; Altamura et al., (1992) J. Mol. Biol. 224:575–587; Koonin, (1992) Trends Biochem. Sci. 17:495–497); 3) identical to NAM7, a nuclear gene that was isolated as a high copy suppressor of mitochondrial RNA splicing mutations (Altamura et al., (1992) J. Mol. Biol. 224:575–587; and 4) partially homologous to the yeast SEN1 gene (Leeds et al., (1992) Mol. Cell. Biol. 12:2165–2177). The latter encodes a noncatalytic subunit of the tRNA splicing endonuclease complex (Winey and Culbertson, (1988) Genetics 118:607–617; DeMarin et al., (1992) Mol. Cell Biol. 12:2154–2164), suggesting that the Upf1p protein (Upf1p) may also be part of a nuclease complex targeted specifically to nonsense-containing mRNAs.

Suppression of nonsense-mediated mRNA decay in upf1 deletion strains does not appear to result simply from enhanced read-through of the termination signal (Leeds et al., (1991) Genes & Devel 5:2303–2314), nor does it appear to be specific for a single nonsense codon. The ability of upf1– mutants to suppress tyr7-1 (UAG), leu2-1 (UAA), leu2-2 (UGA), met8-1 (UAG), and his4-166 (UGA) (Leeds et al., (1992) Mol. Cell Biol. 12:2165–2177) indicates that they can act as omnipotent suppressors. upf1– mutants degrade nonsense-containing transcripts at a slower rate allowing synthesis of sufficient read-through protein to permit cells to grow under nutrient-deficient conditions that are nonpermissive for UPF1+ cells.

SUMMARY OF THE INVENTION

The invention relates to the discovery of a gene, NMD2, named after its role in the Nonsense-Mediated mRNA Decay pathway, and the protein, Nmd2p, encoded by the NMD2 gene. Nmd2p is shown herein to bind to Upf1p. A C-terminal fragment of the protein is also shown to bind Upf1p and, when overexpressed in the host cell, the fragment inhibits the function of Upf1p, thereby inhibiting the nonsense-mediated mRNA decay pathway.

The invention further relates to the inhibition of the nonsense-mediated mRNA pathway to produce a heterologous recombinant protein or polypeptide in a host cell or to increase the production of an endogenous protein useful to a host cell or organism. A codon of the gene encoding the recombinant protein is mutated to encode a nonsense codon. Expression of this recombinant protein is enhanced by stabilizing the nonsense codon-containing mRNA transcript in a host cell in which the nonsense-mediated mRNA decay pathway is inhibited.

The insertion of a nonsense codon into the gene of interest is useful to produce an altered heterologous protein by amino acid substitution at the nonsense codon in a suppressor host strain. Insertion of a nonsense codon further allows the controlled expression of a protein that may be toxic to the cell by controlling the timing of nonsense mediated mRNA decay pathway inhibition. Insertion of a nonsense codon also allows the production of an N-terminal fragment of a heterologous protein in increased yield when the nonsense codon-containing transcript is expressed in a host strain that is not a suppressor of nonsense codons.

It is an object of the invention to increase expression of nonsense codon-containing transcripts by inhibiting the nonsense-mediated mRNA decay pathway by overexpressing the C-terminal fragment of Nmd2p in the same cell that is also expressing the heterologous protein. Overexpression of the C-terminus of Nmd2p is not deleterious to the cell since its expression provides specific stabilization of transcripts having a stop codon early in the transcript and does not affect the stability of other transcripts.

The invention features a method of substantially inhibiting the nonsense-mediated mRNA decay pathway by providing a cell (such as a yeast cell) and mutating the NMD2 gene such that essentially no functional Nmd2p is produced. For example, an insertional mutation which prevents synthesis of the Nmd2p results in an inhibited nonsense-mediated mRNA decay pathway without affecting the viability of the cell as described herein.

The invention features a method of substantially inhibiting the nonsense-mediated mRNA decay pathway by providing a cell (such as a yeast cell) and mutating the UPF1 gene such that essentially no functional Upf1p is produced. For example, an insertional mutation which prevents synthesis of the Upf1p results in an inhibited nonsense-mediated mRNA decay pathway without affecting the viability of the cell as described herein.

The invention features a method of inhibiting the nonsense-mediated mRNA decay pathway by providing a cell and transforming the cell with a vector encoding NMD2 operably linked to regulatory sequences for constitutive or inducible expression of the antisense transcript. Such an antisense transcript hybridizes to essentially all of the NMD2 sense transcript preventing translation and the production of functional Nmd2p, thereby inhibiting the nonsense mediated mRNA decay pathway. By "hybridizing to essentially all of the sense NMD2 transcript" is meant that a sufficient amount of the sense transcript is bound by antisense transcript to inhibit translation such that substantially no functional Nmd2p is produced.

The invention features a method of inhibiting the nonsense-mediated mRNA decay pathway by providing a cell and transforming the cell with a vector encoding UPF1 operably linked to regulatory sequences for constitutive or inducible expression of the antisense transcript. Such antisense transcript hybridizes with essentially all of the UPF1 sense transcript preventing translation production of functional Upf1p, thereby inhibiting the nonsense mediated mRNA decay pathway. By "hybridizing to essentially all of the sense UPF1 transcript" is meant that a sufficient amount of the sense transcript is bound by antisense transcript to inhibit translation such that substantially no functional Upf1p is produced.

The invention also features a substantially pure DNA of the NMD2 gene, and degenerate variants thereof, involved in the nonsense-mediated mRNA pathway of a cell. The DNA of the invention is at least approximately 90% identical to SEQ ID NO:1 at the nucleotide level, and is preferably from the yeast *Saccharomyces cerevisiae*. The DNA encodes an amino acid sequence of Nmd2p (SEQ ID NO:2). The sequence of the invention is at least approximately 90% identical to the amino acid sequence of SEQ ID NO:2 at the amino acid level.

The invention also features the substantially pure DNA sequence of the 3' terminus (SEQ ID NO:3) of NMD2. The 3' terminus encodes the carboxy terminal fragment (SEQ ID NO:4) of Nmd2p, which fragment, when overexpressed in a yeast cell, binds to Upf1p and inhibits the nonsense-mediated mRNA decay pathway.

In addition, the invention features a vector containing a DNA sequence (SEQ ID NO:1) encoding a polypeptide (SEQ ID NO:2). Preferably the coding sequence is under the transcriptional control of regulatory sequences that are activated and deactivated by an externally applied condition such as temperature, or an externally supplied chemical agent. Such controlled expression systems are well known to those of ordinary skill in the art. Thus, the expression of the DNA is turned on and off as necessary for the controlled (i.e. conditional) inhibition of the nonsense-mediated mRNA pathway.

The invention further features a vector containing a DNA sequence (SEQ ID NO:3) encoding a polypeptide (SEQ ID NO:4) which polypeptide, when overexpressed in a cell, inhibits the nonsense mediated mRNA pathway. Preferably the coding sequence is under the transcriptional control of regulatory sequences that are activated and deactivated by an externally applied condition such as temperature or an externally supplied chemical agent, controls expression systems well known to those of ordinary skill in the art. Thus, the expression of the DNA is turned on and off as necessary for the controlled (i.e. conditional) inhibition of the nonsense-mediated mRNA pathway.

The invention also features a host cell containing the DNA of SEQ ID NO:1 or SEQ ID NO:3 or fragments thereof. The invention also features cells harboring vectors containing the DNA of SEQ ID NO:1 or SEQ ID NO:3 or fragments thereof.

The invention features substantially pure nonsense-mediated mRNA decay protein, Nmd2p (SEQ ID NO:2), and fragments thereof from a yeast cell, preferably from the genus Saccharomyces.

The invention also features a substantially pure nonsense-mediated mRNA decay protein Nmd2p C-terminal fragment (SEQ ID NO:4) and fragments thereof which bind to the nonsense-mediated mRNA decay pathway protein, Upf1p, and which when overexpressed in a cell, substantially inhibit nonsense-mediated mRNA decay in the cell.

The invention also features a cell containing a vector expressing a polypeptide containing the Nmd2p carboxy terminal fragment (SEQ ID NO:4), which fragment binds to the nonsense-mediated mRNA decay pathway protein, Upf1p and, when overexpressed in the cell, substantially inhibits nonsense-mediated mRNA decay in the cell.

In addition, the invention features methods of producing a heterologous polypeptide from an mRNA transcript in which the transcript contains at least one nonsense codon within a transcript destabilizing 5' portion. The method involves providing a cell in which the nonsense mediated mRNA decay pathway is substantially inhibited by 1) overexpression of a polypeptide containing the Nmd2p carboxy terminal fragment (SEQ ID NO:4) or 2) mutation of NMD2 or UPF1 (e.g., insertional mutagenesis) resulting in inhibition of the nonsense-mediated mRNA decay pathway of the cell; or 3) expression of NMD2 or UPF1 antisense mRNA which hybridizes to the sense transcript of NMD2 or UPF1, respectively, inhibiting translation and, thereby inhibiting nonsense mediated mRNA decay. Expression in this cell of a nonsense codon-containing gene encoding the heterologous polypeptide provides a transcript whose stability is enhanced at least 2 fold compared to a wild-type cell. Translation of the transcript produces the heterologous polypeptide.

In another embodiment, the invention features antibodies that are raised against and bind specifically to Nmd2p, a protein having the amino acid sequence of SEQ ID NO:2, or a polypeptide having the amino acid sequence of SEQ ID NO:4. The antibodies can be polyclonal or monoclonal.

The invention further features a method of screening a candidate host cell for the presence or absence of 1) Nmd2p, 2) a C-terminal fragment of Nmd2p, 3) a polypeptide of SEQ ID NO:2, or 4) a polypeptide of SEQ ID NO:4, including fragments or analogs thereof. The method also can be used to determine relative amounts of each of the proteins in a cell. The screening method is useful for isolating a host strain in which heterologous protein production is to be optimized. The method first involves lysis of a clonal population of cells suspected of containing Nmd2p or Nmd2p fragment. Antibody to Nmd2p or Nmd2p fragment is contacted with proteins of the lysate. Presence, relative abundance, or absence of Nmd2p or Nmd2p fragment in the lysate is determined by the binding of the antibody. Possible detection methods include affinity chromatography, Western blotting, or other techniques well known to those of ordinary skill in the art.

It is an object of the invention that a heterologous polypeptide produced by the method of the invention can be a desired fragment of a protein or polypeptide. A nonsense codon is incorporated into the DNA sequence encoding the protein or polypeptide at a position within a transcript destabilizing 5' portion of the sequence at a desired transcriptional stop site. Expression of the DNA in a cell having an inhibited nonsense-mediated mRNA decay pathway results in a substantially increased half-life for the nonsense codon-containing transcript. An advantage of this method is the stabilization of the transcript allowing an increased amount of the protein fragment to be produced relative to the amount produced in a wild-type host strain.

As an object of the invention, a heterologous protein that is normally toxic to a cell is produced by controllably inhibiting the nonsense-mediated mRNA decay pathway and thereby, controlling the stability of a nonsense codon-containing transcript for the toxic protein. Inhibition of the nonsense-mediated mRNA decay pathway is accomplished, for example, by the inducible expression of the C-terminus of the Nmd2p only when protein production is desired (e.g., at optimal cell density of the culture). Inhibition of the nonsense-mediated mRNA decay pathway substantially increases the half-life of the transcript containing a nonsense codon in a transcript destabilizing 5' portion of the transcript thereby increasing translation and production of the protein when desired. Preferably, in this feature of the invention, the cell expressing the heterologous protein is a nonsense suppressor cell in which the suppressor mechanism is controllably expressed and substitutes the naturally occurring amino acid at the site of a nonsense codon.

As an object of the invention, an altered heterologous polypeptide is produced in a nonsense suppressor cell by substituting an amino acid at the position of a nonsense codon, which amino acid is not the amino acid naturally occurring at that position. An amino acid is substituted which alters a target biological activity of the protein in the cell. The nonsense-mediated mRNA pathway is inhibited to increase production of the altered heterologous polypeptide from a transcript containing a nonsense codon in a transcript destabilizing 5' portion of the transcript.

Alteration in biological activity includes increased binding affinity to a target molecule such as a receptor, antibody, or decreased toxicity of the protein to the host strain in which the protein is produced. By "substantial reduction in toxicity" is meant that expression of the altered heterologous polypeptide allows the cell growth rate to be at least 2 fold greater than the growth rate in the presence of the natural toxic heterologous polypeptide, or allows sufficient cell growth for production of the altered heterologous protein.

An advantage of the invention is the ability to increase heterologous protein production and direct amino acid substitution to a desired codon position using a nonsense codon and producing the protein in a suppressor mutant such that a known amino acid is substituted in each suppressor host. Stabilization of the mRNA transcript by inhibiting the nonsense-mediated mRNA decay pathway increases the half-life of the transcript (decreases its decay rate) thereby allowing increased translation from the transcript. Preferably the nonsense codon is present in a transcript destabilizing 5' portion of the transcript. Preferably the transcript containing the nonsense codon decays rapidly in the presence of an unaltered wild-type nonsense-mediated mRNA decay pathway, and decays at least 2 fold more slowly in the presence of a nonsense-mediated mRNA decay pathway inhibited by the method of the invention.

By "substantially pure DNA" is meant a DNA that is not immediately contiguous with (i.e., covalently linked to) both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector, into an autonomously replicating plasmid or virus, or into the genomic DNA of a prokaryote or eukaryote ; or which exists as a separate molecule (e.g., a cDNA or a genomic or cDNA fragment produced by PCR (polymerase chain reaction) or restriction endonuclease digestion) independent of other sequences. It also includes a recombinant DNA which is part of a hybrid gene encoding additional polypeptide sequences.

By "polypeptide" is meant any chain of amino acids, regardless of length or post-translational modification (e.g., glycosylation).

By "inhibited nonsense-mediated mRNA decay pathway" is meant decreased turnover of a nonsense codon-containing mRNA transcript in which the half-life of the nonsense codon-containing mRNA is at least 2 fold greater in a nonsense-mediated mRNA decay pathway altered by the methods of the invention relative to its half-life in a wild type cell. Techniques for measuring mRNA half-life are described herein and in Parker R. et al. (1991) Meth. Enzymol. 194:415–423.

By "transcript destabilizing 5' portion" is meant a 5' proximal region of an mRNA transcript in which region the presence of a nonsense codon results in an increased rate of transcript degradation by at least 2 fold compared to the normal transcript in a wild-type organism. Determination of a transcript destabilizing 5' portion is readily performed by one of ordinary skill in the art. The DNA sequence is altered at each of at least three known positions in separate copies of the same DNA to encode a nonsense codon at each position. The half-life the transcript from each altered DNA is compared to the wild-type transcript by standard techniques. An approximately 2 fold or more decrease in half-life for the altered transcript in a cell expressing wild-type nonsense-mediated mRNA decay pathway activity indicates that the nonsense codon is in a transcript destabilizing region. The region 5' proximal of the most downstream destabilizing nonsense codon position is considered a transcript destabilizing 5' portion.

By "Nmd2p" is meant the protein (SEQ ID NO:2) encoded by the *Saccharomyces cerevisiae* gene, NMD2 (SEQ ID NO:1), which is involved in the nonsense-mediated mRNA decay pathway.

By "Upf1p" is meant the protein encoded by the *Saccharomyces cerevisiae* gene, UPF1, which is involved in the nonsense-mediated mRNA decay pathway (Leeds, P. et al. (1992), supra).

By "substantially pure polypeptide" is meant that the nonsense-mediated mRNA decay polypeptide or fragment thereof provided by the invention is at least 60%, by weight, free from the proteins and naturally-occurring organic molecules with which it is naturally associated. Preferably, the preparation is at least 75%, more preferably at least 90%, and most preferably at least 99%, by weight, nonsense-mediated mRNA decay polypeptide or fragment. A substantially pure nonsense-mediated mRNA decay polypeptide or fragment thereof is obtained, for example, by extraction from a natural source by expression of a recombinant nucleic acid encoding a nonsense-mediated mRNA decay polypeptide or fragment thereof; or by chemically synthesizing the polypeptide or fragment. Purity can be measured by any appropriate method, e.g., column chromatography, polyacrylamide gel electrophoresis, or HPLC analysis.

By "carboxy terminal fragment (SEQ ID NO:4) of Nmd2p" is meant the sequence including amino acid 326 to amino acid 1089 (SEQ ID NO:4) or a fragment thereof. The carboxyl terminus is any polypeptide including SEQ ID NO:4 or a fragment thereof that substantially inhibits nonsense-mediated mRNA decay in a cell when the fragment is expressed above endogenous level.

By "substantially inhibit nonsense-mediated mRNA decay" is meant to cause an increase by at least 2 fold in the half-life of an mRNA of interest in the presence of an inhibiting agent (e.g., a chemical agent, a polypeptide fragment, or like substance) that interferes with the functioning of the proteins of the nonsense-mediated mRNA pathway.

By "overexpressed polypeptide" is meant the in vivo expression of a DNA sequence to produce a polypeptide in a quantity at least 2 fold greater than the quantity of the same polypeptide expressed from the endogenous transcription/translation regulatory elements of the DNA sequence of interest. In the case of the expression of a gene fragment, the endogenous regulatory elements are those of the native gene.

By "substantially increased transcript stability" is meant an increase in the half-life of an mRNA transcript by at least 2 fold in the presence of an inhibited nonsense-mediated mRNA decay pathway. The half-life of an mRNA transcript can be measured by extracting at various time points total mRNA from a cell expressing the gene of interest. This is followed by determining the abundance of a transcript over time by Northern analysis using a labelled (e.g., radiolabelled probe) nucleic acid probe to visualize the transcript. Increased transcript stability can also be inferred from increased expression of a polypeptide from the gene of interest in the presence of an inhibited nonsense-mediated mRNA pathway.

By "essentially no functional protein produced" is meant sufficient lack of a particular protein (e.g., Nmd2p or Upf1p) in a cell such that the nonsense-mediated mRNA decay pathway is sufficiently inhibited to result in a substantial increase in the stability of mRNA transcripts containing a nonsense codon in a transcript destabilizing 5' portion such as is described herein for the PGK1 transcript.

By "operably linked" is meant that a gene and a regulatory sequence(s) are connected in such a way as to permit gene expression when the appropriate molecules (e.g., transcriptional activator proteins) are bound to the regulatory sequence(s).

By "inducible regulatory sequences" is meant regulatory sequences (e.g., transcriptional regulatory sequences) whose function is initiated by the introduction of one or more external agents to the cell culture medium and whose function is inhibited by the removal of the external agents.

By "sense transcript" is meant the transcript resulting from expression of the gene-encoding DNA strand from operably linked regulatory sequences. By "antisense transcript" is meant the transcript resulting from expression of the strand complementary to the sense strand from operably linked regulatory sequences. The antisense transcript binds to and inhibits translation of the sense transcript.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

The drawings will first be described. The file of this patent contains at least one drawing executed in color. Copies of this patent with color drawings will be provided by the Patent and Trademark Office upon request and payment of the necessary fee.

Figure 1:
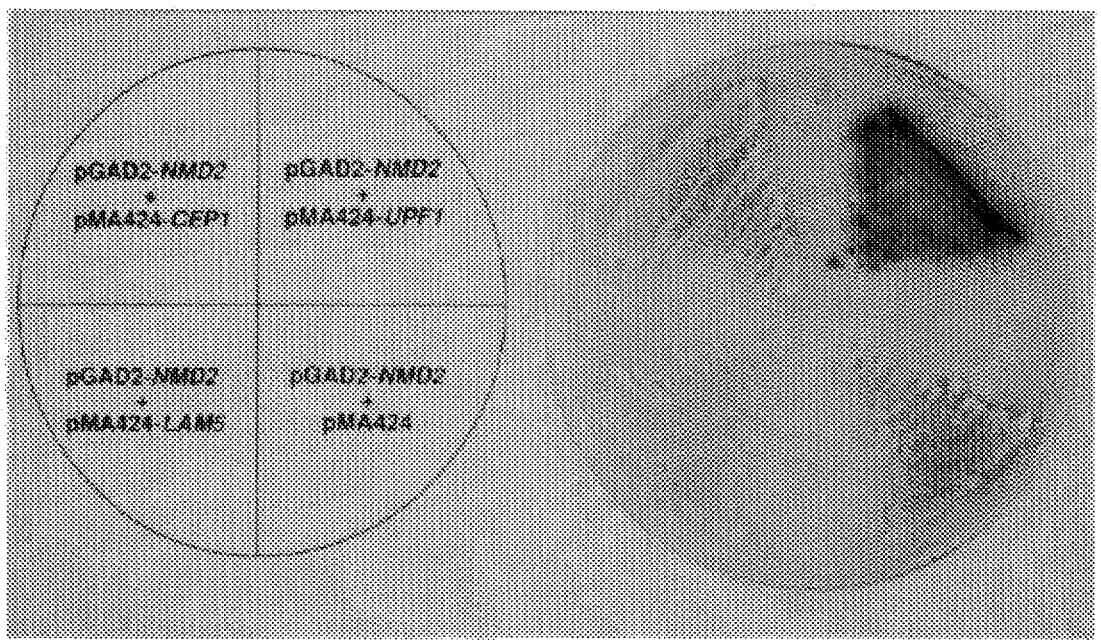

Drawings FIG. 1 is a photograph of yeast colonies on X-Gal medium and a diagram identifying the fusion plasmids contained in the yeast strains for a two-hybrid screening assay. β-galactosidase activity indicates interaction between NMD2 and UPF1 fusion products.

Figure 2A:
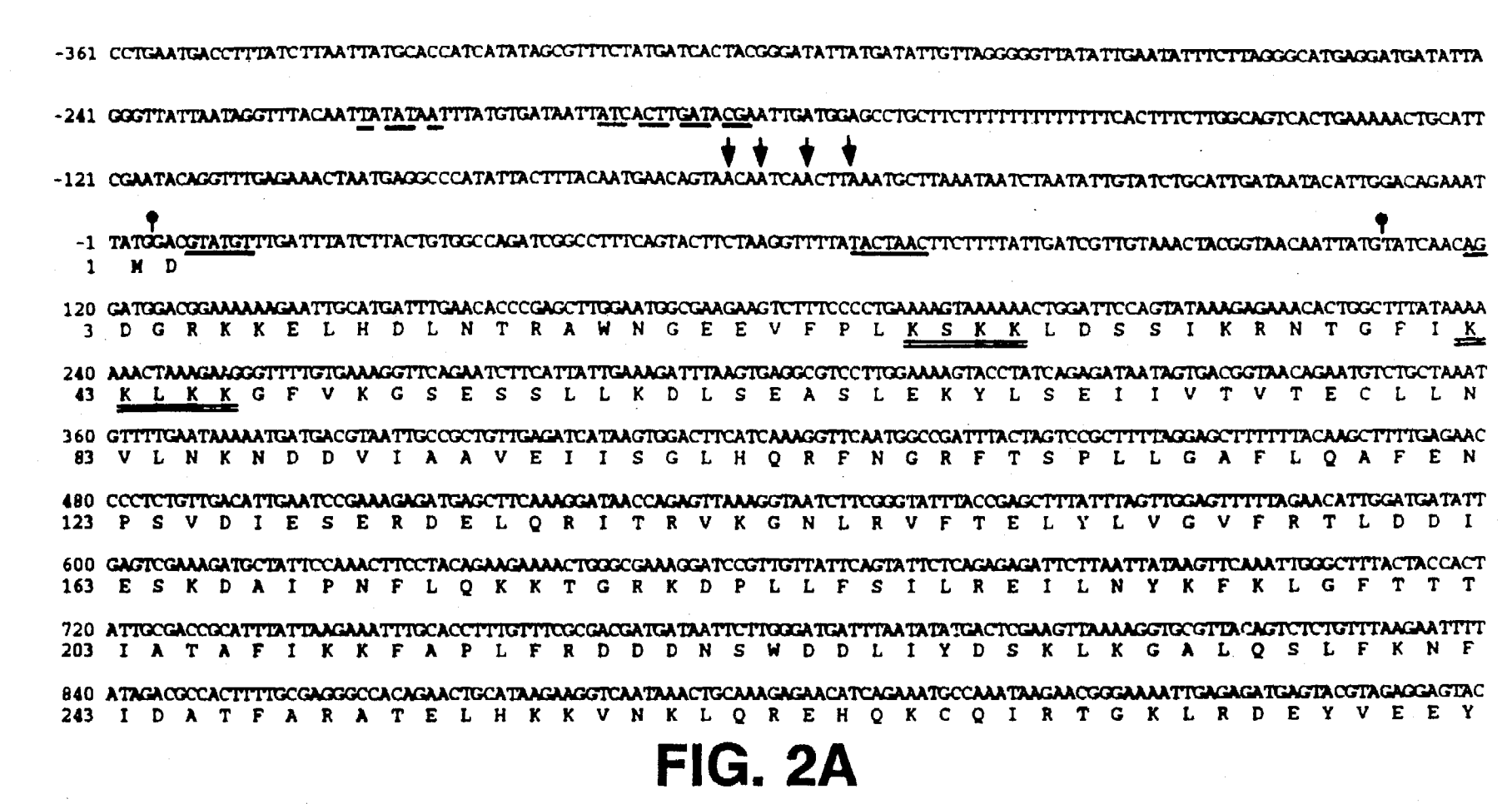
Figure 2B:
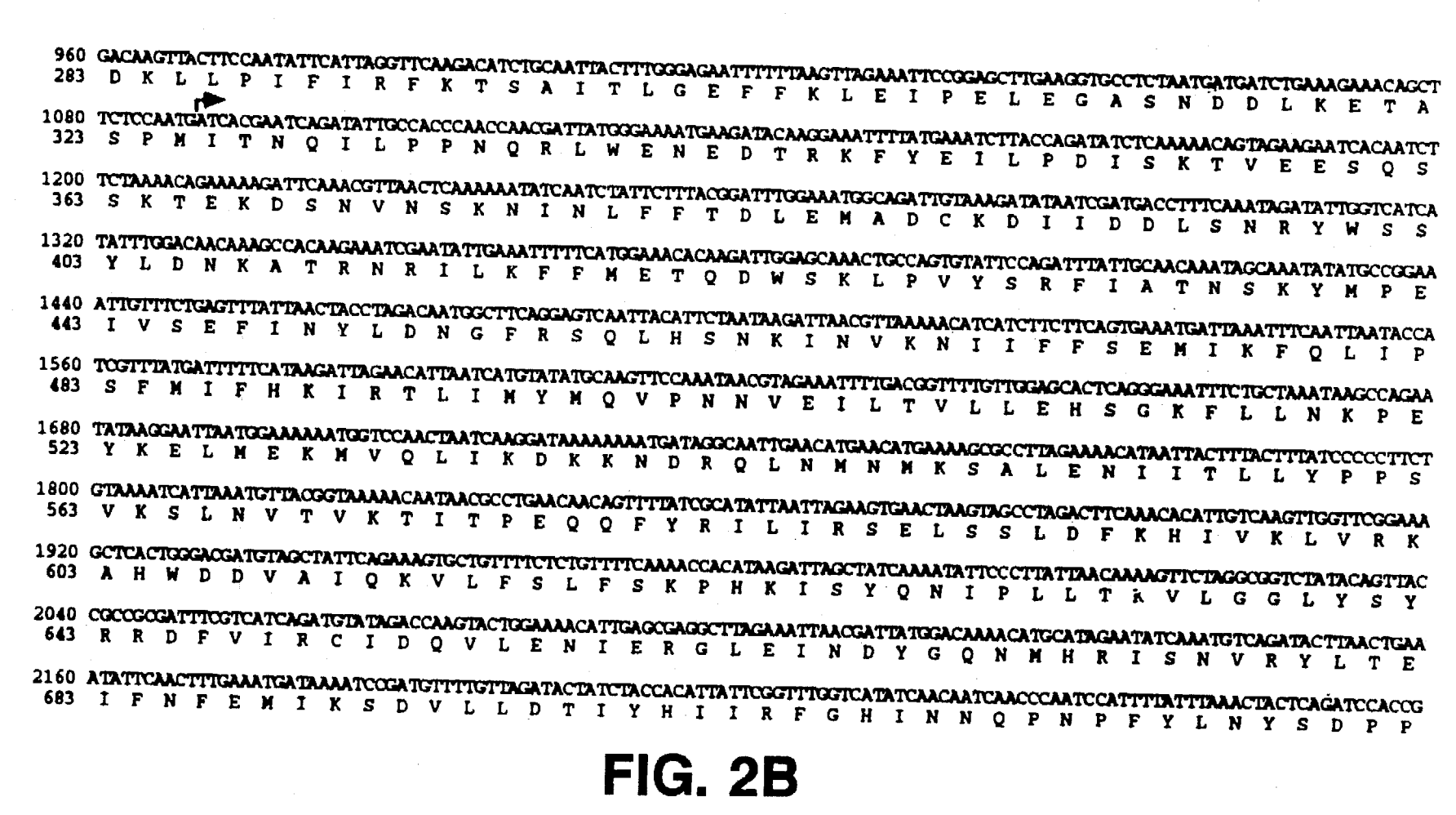

FIG. 2 is the DNA sequence (SEQ ID NO:1) and the deduced amino acid sequence (SEQ ID NO:2) of NMD2. Cloning of the NMD2 gene and determination of its DNA sequence are described herein. The predicted amino acid sequence is indicated in single-letter code and shown below each line of DNA sequence. Position number 1 corresponds to the A of the ATG initiation codon. The NMD2 open reading frame is interrupted by an intron of 113 nucleotides in which the conserved 5' splice site [GUAUGU], branchpoint [UACUAAC], and 3' splice site [AG] are underlined. Transcription initiation sites at nucleotides −56, −60, −64, and −67 (relative to the initiator ATG) were determined by primer extension analysis and are indicated by vertical arrows. The putative TATA box and Abf1p binding consensus sequence, located between positions −219 to −213 and −198 to −186 in the NMD2 promoter region are respectively underlined by dashed lines. Double underlined residues fit the consensus for a bipartite nuclear localization signal (Dingwall and Laskey, (1991) Trends Biochem. Sci. 16:478–481). The positions where FLAG- or MYC-epitope tag sequences were inserted are indicated by lollipops and the position where the original GAL4-NMD2 fusion begins is indicated by an arrow with a right angle stem. The bent arrow also indicates the start of the DNA sequence from nucleotide 1089 to nucleotide 3383 (SEQ ID NO:3) encoding the carboxyl terminal amino acid sequence from amino acid 326 to amino acid 1089 (SEQ ID NO:4) of Nmd2p, a peptide fragment which, when overexpressed, binds to Upf1p and inhibits the nonsense-mediated mRNA decay pathway.

Figure 3A:
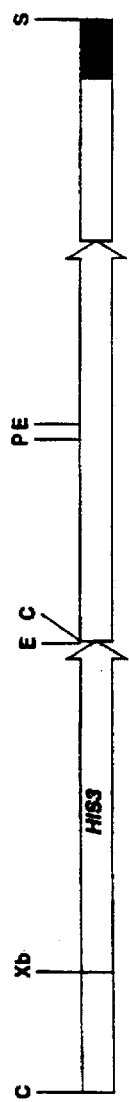
Figure 3B:
Figure 3C:
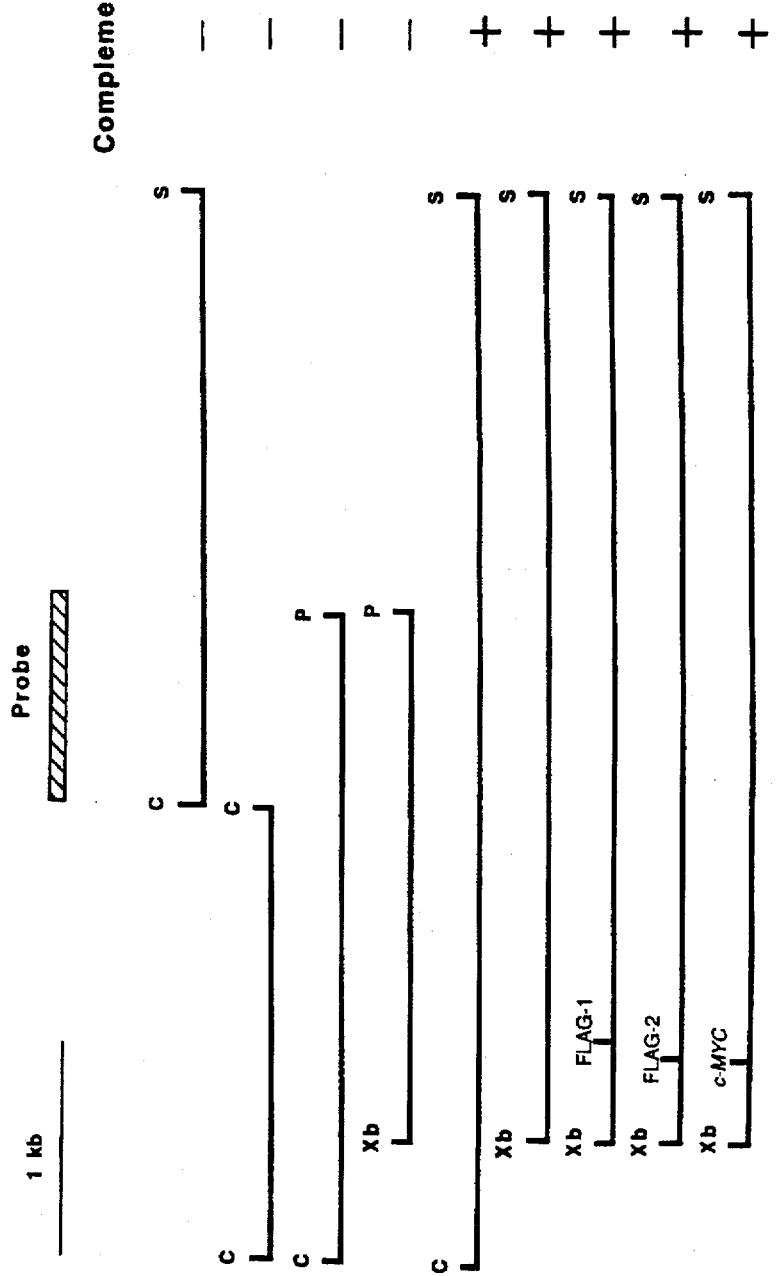

FIGS. 3A to 3C are diagrams of insertion and deletion experiments performed to assess the active regions of NMD2 gene. DNA fragments associated with NMD2 function are indicated. FIG. 3A is a restriction map of the nmd2::HIS3 allele. FIG. 3B is a restriction map of the NMD2 gene. FIG. 3C is a diagram of the results of a complementation analysis to determine functional portions of Nmd2p.

Figure 4A:
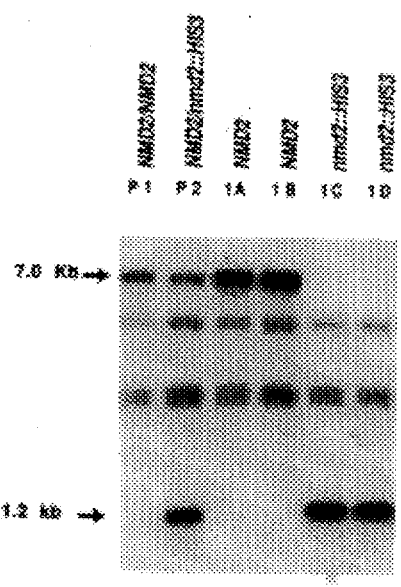
Figure 4B:
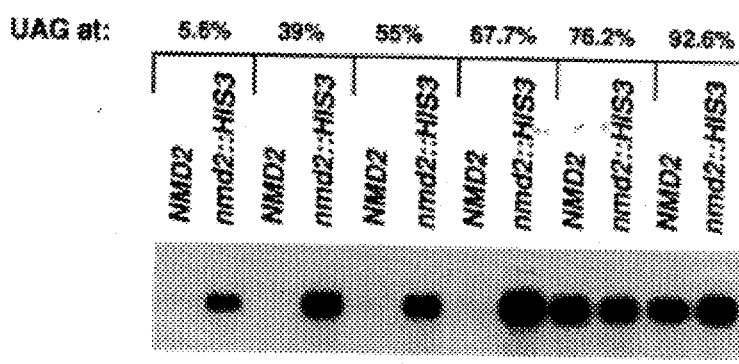
Figure 4C:
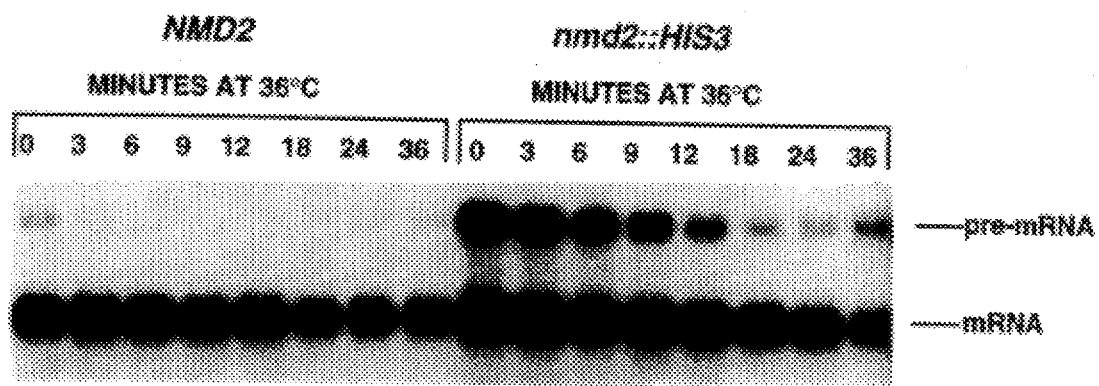

FIGS. 4A to 4C are reproductions of autoradiograms. FIG. 4A is reproduced from a Southern analysis of wild type and HIS3-disrupted NMD2 associated with NMD2 gene disruption. FIG. 4B is reproduced from a Northern analysis of the stability of different nonsense-containing PGK1 alleles in NMD2 and nmd2::HIS3 haploid yeast strains. FIG. 4C is reproduced from a Northern analysis of CYH2 pre-mRNA and mRNA transcript stability.

Figure 5A:
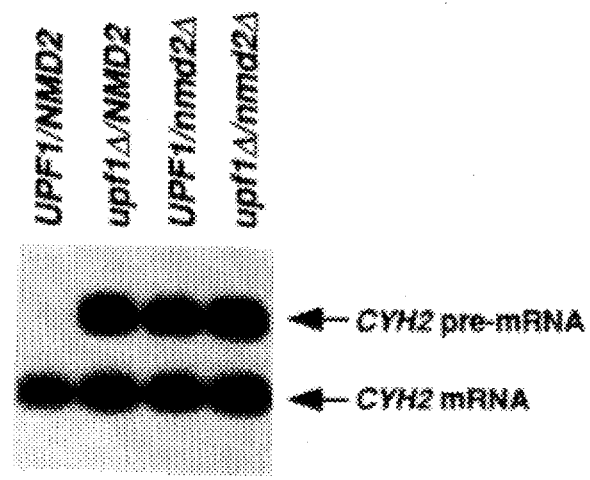
Figure 5B:
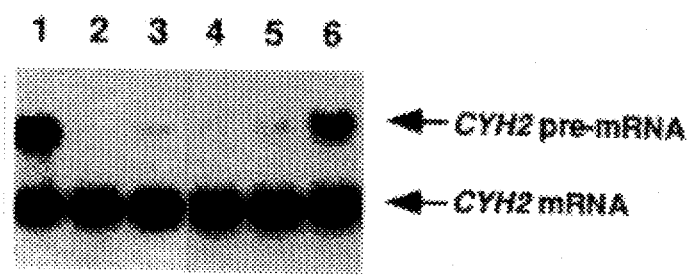

FIGS. 5A to 5B are reproductions of Northern analysis autoradiograms which record the CYH2 transcript stability phenotypes associated with disruption of both the NMD2 and UPF1 genes or overexpression of Nmd2p fragments.

This invention relates to a DNA sequence, a protein, and methods useful in inhibiting the nonsense-mediated mRNA decay pathway in a cell, preferably in a yeast cell, thereby stabilizing an mRNA transcript which contains a nonsense codon. Preferably, the nonsense codon is in a transcript destabilizing 5' portion of the transcript. Stabilization of the transcript allows increased translation and increased production of a heterologous protein of interest. The protein of interest can be a full length protein if the nonsense codon is suppressed. The protein of interest can be a desired N-terminal fragment of a protein if the nonsense codon is not suppressed.

EXAMPLES

The current invention is illustrated by the following examples, which are not to be construed as limiting in any way. The examples illustrate the invention by describing the NMD2 gene, the Nmd2protein, and its C-terminal fragment. Methods of substantially inhibiting the nonsense-mediated mRNA decay pathway in a cell, and methods of producing heterologous proteins and fragments of proteins are also described. These methods inhibit the nonsense-mediated mRNA decay to increase transcript stability.

EXAMPLE 1

Identification of a Gene Encoding a Putative Upf1p-interacting Protein

To identify a gene or genes encoding putative Upf1p-interacting proteins, the yeast two-hybrid system was used. This method of detecting protein-protein interactions in yeast is based on the observation that the DNA binding and transcriptional activation functions of the GAL4 protein (Gal4p) can reside on two distinct chimeric polypeptides and still activate transcription from a GAL UAS, provided that the two polypeptides can interact with each other (Fields and Song, (1989) Nature 340:245–246; Chien, C.-T. et al., (1991) Proc. Natl. Acad. Sci. 88:9578–9582). As employed herein, the first hybrid was cloned into a plasmid (such as pMA424; (Ma, J. and Ptashne, M. (1988) Cell 55:443–446) in which the entire UPF1 coding region was fused in-frame to the Gal4p DNA binding domain (amino acids 1-147 of Gal4p). Construction of plasmid pMA424-UPF1 was performed by a three-fragment ligation. A fragment of 144 bp from the initial ATG codon to the 48th codon of UPF1 was amplified by the polymerase chain reaction (PCR) using UPF1-TH-5' (SEQ ID NO:5) and UPF1-TH-3' (SEQ ID NO:6) as oligonucleotide primers (Table 1).

TABLE 1

| Oligonucleotide Primers | | |
|---|---|---|
| UPF-TH-5' | 5'-CCGGAATTCATGGTCGGTTCCGGTTCT-3' | (SEQ ID NO: 5) |
| UPF-TH-3' | 5'-AGTGACTTGAGCCTC-3' | (SEQ ID NO: 6) |

Amplification with these primers led to the introduction of an EcoRI site adjacent to the initiator ATG. The PCR-amplified fragment was digested with EcoRI and BstXI and ligated with a BstXI-BamHI fragment (including the rest of the UPF1 coding region and approximately 1 kb 3' distal to the translational termination site including the entire 3' UTR) into plasmid pMA424 digested by EcoRI and BamHI. DNA sequence analysis confirmed the primary structure of the construct.

Second hybrids were encoded by *S. cerevisiae* genomic DNA libraries in plasmids pGAD(1-3) (Chien, C.-T. et al. (1991) Proc. Natl. Acad. Sci USA 88:9578-9582) fused, in the three reading frames, to sequences encoding the Gal4p transcriptional activation domain (amino acids 768-881). Both were cotransformed into a *Saccharomyces cerevisiae* strain that contained an integrated GAL1-LacZ reporter construct (such as the *S. cerevisiae* strain GGY1::171 (Δgal4 Δgal80 URA3::GAL1-LacZ his3 leu2)) (Gill, G. and Ptashne, M. (1987) Cell 51:121-126) or equivalent strain well known to those of ordinary skill in the art of yeast genetics.

In performing the two-hybrid screening method, the GGY1::171 yeast strain was cotransformed with both pMA424-UPF1 and a library containing genomic DNA fragments fused to the GAL4 activation domain. After 3-4 days of growth on SD-His-Leu plates at 30° C., His$^+$Leu$^+$ transformants were replica-plated to SSX plates and were incubated until blue colonies appeared as described in Rose, M. D. et al. (1990) *Methods in Yeast Genetics: A Laboratory Course Manual*, Cold Spring Harbor Laboratory, Cold Spring Harbor, N.Y.). False positive colonies due to cloning of the GAL4 gene into the pGAD vectors were eliminated by PCR yeast cellular DNA using the GAL4-specific primers GAL4-5' (from nucleotide 1206 to 1229 of the GAL4 gene) and GAL4-3' (from nucleotide 2552 to 2528 of the GAL4 gene) (Laughon and Gesteland, (1984) Mol. Cell Biol. 4:260-267). Cells from the remaining blue colonies were grown in SD-Leu medium and plasmids were recovered and transformed into the *E. coli* strain MH6 by electroporation. The activation domain (pGAD) plasmids from the library were identified by their ability to complement an *E. coli* leuB mutation due to the presence of the plasmid-borne LEU2 gene. According to the two-hybrid test, transcriptional activation depends interaction between the UPF1 fusion product and the test fragment fusion product. To confirm that transcriptional activation was dependent on the presence of both gene fusions, the isolated library plasmids were retransformed into the original GGY1::171 strain with either: 1) pMA424-UPF1, a GAL4 DNA-binding domain-UPF1 fusion plasmid; 2) pMA424, the GAL4 DNA binding domain vector only; 3) pMA424-CEP1, a GAL4 DNA-binding domain-CEP1 fusion plasmid; or 4) pMA424-LAM5, a GAL4 DNA-binding domain-LAM5 fusion plasmid, where CEP1 and LAM5 genes are negative control genes whose gene products are known not to bind to UPF1 gene product. Plasmids that yielded blue colonies only with the pMA424-UPF1 fusion were characterized further by restriction mapping, Southern analysis, and sequence analysis (see e.g., Sambrook et al., (1989), *Molecular Cloning: A Laboratory Manual*, Cold Spring Harbor Laboratory Press, Cold Spring Harbor, N.Y.). DNA sequences were compared to existing sequence databases using the FASTA program (Devereux, J. et al., (1984) Nucleic Acids Res. 12:387-395). Colonies expressing detectable β-galactosidase activity were sought by screening approximately 400,000 transformants.

Eighty-seven colonies that demonstrated β-galactosidase activity (i.e., colonies pale blue to dark blue on X-Gal plates) on the initial screen were isolated. Because the libraries were constructed using genomic DNA from a GAL4 wild-type strain, plasmids containing the GAL4 gene, or fragments thereof, are capable of activating transcription of the GAL1-LacZ reporter gene. These false positive colonies were eliminated by use of the polymerase chain reaction (PCR; White, T. J. et al., (1989) Trends Genet. 5:185-189) with GAL4 specific primers. The library plasmids from the remaining colonies were rescued and tested for specificity by retransforming them into the original strain with either: 1) the GAL4-UPF1 fusion; 2) the GAL4 DNA binding domain vector only; 3) an unrelated fusion, GAL4-CEP1; or 4) an unrelated fusion, GAL4-LAM5 (Bartel, P. et al., (1993) Biotechniques 14:920-924). Forty-two plasmids that yielded blue colonies only with GAL4-UPF1 fusion plasmid-containing strains were characterized further by restriction mapping, Southern analysis, and partial DNA sequence analysis using standard techniques (see e.g., Sambrook, J. et al., (1989) supra.

FIG. 1 shows the blue colony formation that occurred only when NMD2 and UPF1 fusion plasmids were present in the same host strain. The *S. cerevisiae* tester strain GGY1::171 was co-transformed with the original library isolate pGAD2-NMD2 and one of the following plasmids: 1) pMA424-UPF1, 2) pMA4242, 3) pMA424-CEP1, or 4) pMA424-LAM5 (pMA424-CEP1 was obtained from Richard Baker of the University of Massachusetts Medical Center, Worcester, Mass.; pMA424-LAM5 was obtained from Stanley Fields and Paul Bartel of State University of New York, Stony Brook, N.Y. Individual Leu$^+$ His$^+$ transformants were selected and streaked on synthetic medium plates lacking histidine and leucine. β-galactosidase activity assays were performed by replica-plating the transformants onto SSX plates containing X-Gal. Cells were incubated at 30° C. for 24-48 hours for development of blue color.

Southern blot analysis of the isolated plasmids was performed by first extracting total yeast genomic DNA according to the method of Holm, C. et al. (1986) Gene 42:169-173. After restriction digestion, DNA was electrophoresed on 0.8% agarose gels, transferred and crosslinked to Zetaprobe membranes (BioRad, Richmond, Calif.) as described in Sambrook, J. et al. (1989), supra. Filters were prehybridized 2-3 hours at 42° C. in 5× SSPE, 40% formamide, 5× Denhardt's solution, 0.1% SDS, and 4 mg/ml salmon sperm DNA. A radiolabeled NMD2 probe (1.2 kb ClaI-EcoRI fragment), generated by random priming, was added and filters were hybridized overnight at 42° C. Filters were washed twice in 1× SSC, 0.1% SDS at room temperature and once in 0.1× SSC, 0.1% SDS at 58° C. before analyzing on a Betagen Blot Analyzer (Herrick, D. et al., (1991) Mol. Cell. Biol. 10:2269-2284).

DNA sequences were determined by the method of Sanger, F. et al., (1978) Proc. Natl. Acad. Sci. 74:5463-5467. Overlapping fragments of the NMD2 gene were subcloned in Bluescript and sequenced by annealing oligonucleotide primers specific to the T3 or T7 promoter regions of the plasmid or by using oligonucleotide primers which annealed within the subcloned inserts.

Nine different genes were isolated by the following procedure. An *S. cerevisiae* genomic DNA library of Sau3A partial fragments constructed in YCp50 was used (Rose, M. et al. (1987) Gene 60:237-243). Colony hybridization was performed as described in Sambrook, J. et al., (1989), supra, using the same conditions described for the genomic DNA Southern hybridization. Approximately three genomic equivalents were screened. Disruption of the NMD2 gene was performed by transforming the diploid strain W303 (MATa/MATα ade2-1/ade2-1 his3-11,15/his3-11,15 leu2-3, 112/leu2-3,112 trp1-1/trp1-1 ura3-1/ura3-1 can1-100/can1-100) with a SacI-SalI fragment from Bs-nmd2::HIS3 and selecting His$^+$ transformants (the SacI and SalI sites are in the polylinker of the Bluescript KS$^+$ cloning vector, Stratagene, La Jolla, Calif.; Rothstein, R. (1991) "Targeting, disruption, replacement, and allele rescue: integrative DNA transformation in yeast.", in *Methods in Enzymology* 194:

*Guide to Yeast Genetics and Molecular Biology*, C. Guthrie and G. Fink, eds., Academic Press, pp. 281–301; Thomas, B. J. and Rothstein, R. (1989) Cell 56:619–630). The disruption event was confirmed by Southern analysis. Sporulation and tetrad analysis yielded haploid strains containing nmd2::HIS3 disruptions.

Six of the isolated genes encoded putative Upf1p-interacting proteins because their activity in the assay was dependent on fusion to the GAL4 activation domain. The remaining three genes did not require the presence of the GAL4 activation domain, were likely to possess their own activation domains and nuclear localization signals and were not examined further.

Six genes were found to encode putative Upf1p-interacting proteins; two genes are identical to previously characterized yeast genes, i.e., DBP2, a gene encoding a putative RNA helicase with homology to the mammalian p68 RNA helicase (Iggo, R. D. et al., (1991) Mol. Cell. Biol. 11:1326–1333). The other four have no apparent homologues in the available data bases. One of the genes, herein named NMD2, is characterized herein, and its uses for the production of heterologous proteins in yeast are disclosed.

EXAMPLE 2

Molecular Cloning of the NMD2 Gene

As defined by a qualitative β-galactosidase assay, Nmd2p showed a specific dependency on Upf1p in the two-hybrid system. Cells expressing a GAL4 activation domain-NMD2 fusion demonstrated strong β-galactosidase activity when simultaneously expressing a GAL4 DNA-binding domain-UPF1 fusion, but had no detectable β-galactosidase activity when co-transformed with plasmids encoding only the GAL4 DNA-binding domain-LAM5 fusion (FIG. 1). Further evidence for the specificity of the interaction(s) was obtained by analyzing the effects of specific deletions within the UPF1 portion of the GAL4 DNA-binding domain-UPF1 fusion. Deletions in all but one segment of the UPF1 coding region eliminated Nmd2p-Upf1p interaction in the two-hybrid assay.

The GAL4 activation domain-NMD2 plasmid recovered in the two hybrid screen contained only a fragment of the NMD2 gene. To isolate the entire gene, a 1.2 kb ClaI-EcoRI fragment downstream of the GAL4 activation domain in the fusion plasmid was used to screen a yeast YCp50 genomic DNA library (Rose, M. et al., (1987) supra). Two independent clones with identical restriction patterns were isolated.

By restriction mapping, Southern analysis, and subsequent testing for complementation of an NMD2 chromosomal deletion, the NMD2 gene was localized to a 5.2 kb XbaI-SalI DNA fragment as shown in FIGS. 3A to 3C.

A restriction map of the nmd2::HIS3 allele is shown in FIG. 3A. The XbaI-ClaI fragment of the NMD2 gene, was deleted and replaced with the yeast HIS3 gene. The left arrow in FIG. 3A represents the HIS3 gene and indicates the direction of transcription. The right arrow of FIG. 3A represents the NMD2 open reading frame.

A restriction map of the NMD2 gene is shown in FIG. 3B. The NMD2 open reading frame and direction of transcription are indicated by an open arrow interrupted by a stippled box that indicates the position of the intron. The box labeled probe indicates the DNA fragment used for screening the genomic DNA library. In FIGS. 3A and 3B, the black box represents a segment from the cloning vector YCp50 and the restriction site abbreviations are: B, BamHI ; C, ClaI; E, EcoRI; H, HindIII; P, PstI; S, SalI; Xb, XbaI.

To determine the regions of Nmd2p required for complementation of a disrupted nonsense mediated mRNA pathway in a nmd2::HIS3 strain, deletion experiments were performed. In FIG. 3C, lines represent DNA fragments which were subcloned into an appropriate vector (such as pRS315). These constructs were transformed into the yeast strain HFY1300, or equivalent, which contains a partial chromosomal deletion of NMD2 and lacks nonsense-mediated mRNA decay activity (see also, FIGS. 4A and 4B). Total RNA was isolated from these transformants and Northern analysis was performed using a radiolabeled probe derived from the CYH2 gene (He, F. et al., (1993) Proc. Natl. Acad. Sci. 90:7034–7039). Complementing activity was scored by measuring the relative abundance of the CYH2 pre-mRNA and mRNA in each strain. (+) and (−) indicate the ability or inability, respectively, to complement the NMD2 chromosomal deletion, i.e., to restore the CYH2 pre-mRNA to the marginally detectable levels characteristic of wild-type cells (He, F. et al., (1993) Proc. Natl. Acad. Sci. 90:7034–7039).

To obtain a physical map position for the NMD2 gene, the 1.7 kb XbaI-ClaI fragment was used to probe PrimeClone blots (American Type Culture Collection, Rockville, Md.) containing characterized fragments of most of the *S. cerevisiae* genome (ATCC accession number 7155) known to lie on the right arm of chromosome VIII (Riles, L. et al., (1993) Genetics 134:81–150). This fragment is located between the put2 and CUP1 loci at a map position approximately 260 kb from the left telomere (Riles et al., (1993) supra).

EXAMPLE 3

Determining the Primary Sequence of the NMD2 Gene

The complete sequence of the NMD2 gene was determined (SEQ ID NO:1). The NMD2 coding region is 3267 nucleotides in length, encoding an acidic (predicted pI=4.8) protein of 1089 amino acid residues (SEQ ID NO:2) with a predicted molecular weight of 127 kD. This interpretation of the NMD2 sequence relies on the prediction of a 113-nucleotide intervening sequence that commences at position +7 and divides the gene into two exons (FIG. 2).

Four observations support the existence of this intron. First, the sequence contains all three of the standard consensus sequences expected of an intron (5' splice site [GUAUGU], branchpoint [UACUAAC], and 3' splice site [AG]) (FIG. 2). Second, as is true for most introns in yeast (Fink, G. R. (1987) Cell 49:5–6), this intron is located at the 5' end of the NMD2 gene (six nucleotides downstream from the predicted initiator ATG; FIG. 2). Third, specific primer extension products were detected by using two different oligonucleotide primers complementary to mRNA sequences downstream of the predicted 3' splice site, but not by using a primer complementary to sequences within the intron. Finally, using the FLAG or c-MYC epitope tags (Hopp, T. P. et al., (1988) Biotechnology 6:1204–1210; Prickett et al., (1989); Evan, G. I. et al., (1985) Mol. Cell. Biol. 5:3610–3616) and epitope-specific monoclonal antibodies, the expression of a 127 kD polypeptide was detected when the FLAG or c-MYC sequences were inserted adjacent to the putative initiator ATG (FLAG-2-NMD2 or c-MYC-NMD2 alleles), but not when the FLAG sequence was inserted adjacent to the second ATG (FLAG-1-NMD2 allele). The second ATG is located within the putative intron, 37 nucleotides downstream of the predicted intron branchpoint, and is in frame with the major downstream open reading frame but not with the first ATG. It is important to note that both the FLAG-1-NMD2 and FLAG-2-NMD2 alleles are functional in that they both show wild-type ability to complement a chromosomal deletion of NMD2 (FIG. 3C). These results indicate that the FLAG-1 sequence inserted downstream of the second ATG has been removed by splicing out of the putative intron in the NMD2 gene.

Analysis of the NMD2 transcript was consistent with the predicted open reading frame. Northern analysis of total cellular RNA, using the NMD2 XbaI-ClaI fragment as a probe, identified a transcript of approximately 3.6 kb in size. Multiple transcription initiation sites were mapped to positions −56, −60, −64, and −67 using primer extension analysis (see e.g., Boorstein, W. R. and Craig, E. A. (1989) Meth. Enzymol. 180:347–369). A putative TATA box, required for most RNA polymerase II transcription (Struhl, K. (1987) Cell. 49:295–297), lies at positions −219 to −213 in the NMD2 promoter region and another regulatory element, an Abf1p binding consensus sequence (Della Seta, F. et al., (1990) J. Biol. Chem. 265:15168–15175), is located within positions −198 to −186 (FIG. 2).

Structural features of the NMD2 protein (Nmd2p ; SEQ ID NO:2) inferred from the sequence analysis include a highly acidic internal fragment (36.8% aspartic acid and 25.6% glutamic acid) from residues 843 to 975 near the C-terminus and a possible bipartite nuclear localization signal at the N-terminus of the protein (i.e., within residues 26 to 29 and 42 to 46) (FIG. 2 Dingwall and Laskey, (1991) supra). Comparison of the Nmd2p sequence with those in the Swissprot and Pir protein sequence databases using the FASTA or TFASTA comparison programs (Devereux et al., (1984) supra) did not reveal any extensive identity with known protein sequences. However, three domains of Nmd2p have substantial similarity to regions of other proteins. The first domain, spanning Nmd2p amino acids 1 to 390, has 17.7% sequence identity and 47% similarity with translational elongation factor 2 (Eft1p and Eft2p) from S. cerevisiae (Perentesis, J. P. et al., (1992) J. Biol. Chem. 267:1190–1197). The second domain, from amino acids 400 to 810 in Nmd2p, shares 19.5% sequence identity and 42.6% similarity with the S. cerevisiae mitochondrial RNase P protein Rpm2p (Dang, Y. and Martin, N. C. (1993) J. Biol. Chem. 268:19791–19796). The third domain, encompassing the acidic stretch from amino acids 820 to 940, has 34% sequence identity and 63.2% similarity with human and mouse nucleoproteins (Lapeyre, B. et al., (1987) Proc. Natl. Acad. Sci. 84:1472–1476; Bourbon, H-M et al., (1988) J. Mol. Biol. 200:27–638) and 34% identity and 65% similarity to the mammalian polymerase I transcriptional factors hUBF and mUBF (Jantzen, H-M et al., (1990) Nature 344:830–836; Hisatake, K. et al., (1991) Nucleic Acids Res. 19:4631–4637). In hUBF and mUBF this domain has been shown to be important for interaction with other proteins (Jantzen et al., (1990) supra) and, as described below, is also true for Nmd2p.

EXAMPLE 4

NMD2 Disruption Does Not Affect Cell Viability and Selectively Stabilizes Nonsense-containing mRNAs A NMD2 gene disruption experiment was performed to assess the cellular requirement for Nmd2p. The nmd2::HIS3 disruption described in FIG. 3A was constructed. Plasmid Bs-nmd2::HIS3 encodes the same NMD2 disruption and contains a 0.6 kb ClaI-XbaI fragment in the 5'-end of NMD2, a 1.7 kb XbaI-ClaI fragment of HIS3 and a 1.2 kb ClaI-EcoRI fragment in the NMD2 coding region in Bluescript. A SacI-SalI fragment carrying the nmd2::HIS3 allele was isolated from plasmid Bs-nmd2::HIS3 and used to transform the yeast diploid strain W303 for homologous recombination into one of the NMD2 alleles. His⁺ transformants were sporulated and tetrads were individually dissected. Four viable spores were obtained from each tetrad analyzed. Genomic DNAs from parental diploid and progeny haploid strains were isolated, digested with EcoRI. Confirmation of integration is shown by the Southern analysis of FIG. 4A in which lane P1 contains DNA isolated from the homozygous NMD2/NMD2 diploid strain W303; lane P2 contains DNA isolated from a diploid nmd2::HIS3 /NMD2 His⁺ transformant of W303 (HFY1000) ; and lanes 1A to 1D contain DNA isolated from the progeny of four viable spores dissected from the same tetrad represent the wild-type and disrupted alleles of NMD2, respectively. Other bands in the figure are not specific to NMD2.

Haploid strains containing the nmd2::HIS3 disruption were compared to isogenic NMD2 strains for their ability to grow on different carbon sources (glucose, galactose, and glycerol) at temperatures ranging from 18° C. to 37° C. and no differences in growth rates were detected between mutant and wild-type strains. These data indicate that NMD2 is nonessential for cell viability. Since disruption of the NMD2 gene was not lethal, the activities of the nonsense-mediated mRNA decay pathway in both NMD2 and nmd2::HIS3 strains were compared.

The following method was used to analyze transcript stability in strains having an NMD2 disruption, and is useful to one of ordinary skill in the art for analyzing the stability of any transcript of interest. Yeast centromere plasmids carrying six different PGK1 nonsense alleles were constructed previously (Peltz, S. W. et al., (1993) supra). These plasmids were transformed into NMD2 and nmd2::HIS3 strains and the abundance of PGK1 nonsense-containing mRNAs was assessed by Northern analysis as shown in FIG. 4B. Disruption of the NMD2 gene stabilizes PGK1 mRNAs containing early nonsense mutations. Isogenic NMD2 and nmd2::HIS3 haploid yeast strains harboring different nonsense-containing PGK1 alleles (HFY1201 to HFY1206 and HFY1301 to HFY1306)were constructed by transforming HFY1200 and HFY1300 with each of the six plasmids harboring the nonsense-containing PGK1 alleles described previously (Peltz, S. W. et al., (1993) Genes & Devel 7:1737–1754) and herein incorporated by reference.

Total RNA was isolated from these strains and analyzed by Northern blotting using a radiolabeled oligonucleotide probe complementary to the tag sequence located in the 3' untranslated region of PGK1 nonsense-containing mRNAs (Peltz, S. W. et al., (1993) Genes & Devel 7:1737–1754). The location of the nonsense mutation in each PGK1 transcript is presented as a percentage of the PGK1 protein-coding region that is translated before the mutation is encountered (Peltz, S. W. et al., (1993) Genes & Devel 7:1734–1754).

Decay rates of mRNA were measured as previously described (Herrick et al., (1990) ; Parker, R. et al., (1991) Meth. Enzymol. 194:415–423; Peltz, S. W. et al., (1993) supra). For measurement of mRNA abundance, yeast cells (20 ml) were grown to $OD_{600}$=0.5–0.7 at 24° C. for 30 min. An aliquot (2 ml) of cell culture was collected and frozen quickly on dry ice. Total yeast RNA was isolated as described previously (Herrick et al., (1991) supra). For both decay rate measurements and abundance measurements equal amounts (usually 20 μg) of total RNA from each sample were analyzed by Northern blotting, generally using probes labeled in random priming reactions (see, e.g., Sambrook, J. et al., (1989) Molecular Cloning: A Laboratory Manual, 2nd ed., Cold Spring Harbor Laboratory Press, Cold Spring Harbor, N.Y.). Hybridization conditions for such blots were as described for genomic Southern hybridization. When oligonucleotide probes were used, the hybridization conditions were those described by Peltz, S. W. et al. (1993) supra. Northern blots were quantitated with a Betagen Blot Analyzer (Herrick et al., (1990) supra).

Nonsense mutations in the 5' two-thirds of the PGK1 coding region reduced the abundance of the corresponding mRNAs 5- to 20-fold (Peltz, S. W. et al., (1993) supra). The abundance of PGK1 mRNAs with nonsense mutations in the downstream third of the coding region is unaffected. Disruption of the NMD2 gene restored wild-type levels to all four of the PGK1 transcripts normally subject to nonsense-mediated mRNA decay (FIG. 4B). As a control, the abundance of the wild-type PGK1 and ACT1 mRNAs, and the half-life of the MATα1 mRNA in the same cells, was found to be unaffected by the nmd2::HIS3 disruption.

Northern analysis was also used to measure the relative abundance of the CYH2, RP51B, and MER2 pre-mRNAs in NMD2. As shown in FIG. 4C, decay rates of CYH2 pre-mRNA and mRNA were determined by Northern analysis of RNAs isolated at different time points after transcription was inhibited by shifting cultures of isogenic NMD2 (HFY2206) and nmd2(HFY2106) strains to 36° C. Samples were taken for 36 min and the blot was hybridized with a radiolabeled CYH2 DNA probe. To construct strains HFY2206 and HFY2106, stain HFY2000 was produced by integrative transformation; selected and tested to contain the temperature sensitive rpb1-1 allele. Strain HFY2000 was transformed with pRS315 (or similar yeast shuttle plasmid; (Sikorski and Hieter, (1989) Genetics 122:19–27) or pRS315-NMD2 (X-S) (containing a 5.2 kb XbaI-SalI fragment of NMD2 in pRS315) and a plasmid harboring a PGK1 allele with a nonsense mutation at the BglII site (Peltz, S. W. et al., (1993) Genes & Devel 7:1737–1754). The abundance of the inefficiently spliced CYH2 and RP51B pre-mRNAs, and the MER2 pre-mRNA (whose splicing is regulated by MER1; Engebracht et al., 1991) was markedly increased in strains carrying the nmd2::HIS3 disruption. Disruption of the NMD2 gene reduces the decay rate of the CYH2 pre-mRNA approximately four-fold, i.e., from a half-life of 1.5 min to a half-life of 6.0 min without a concomitant effect on the half-life of the CYH2 mRNA (FIG. 4C). These results are equivalent to those obtained in UPF1 knockout strains (He et al., (1993) supra) indicating that Nmd2p is a Upf1p-interacting protein and that NMD2 is a novel component of the nonsense-mediated mRNA decay pathway.

EXAMPLE 5

Overexpression of Truncated Nmd2p in the Cytoplasm Results in a Dominant-negative Nonsense-mediated mRNA Decay Phenotype The region of Nmd2p that interacts with Upf1p was determined by generating 5' and 3' deletions of the original NMD2 fragment, fusing them in-frame to the GAL4 activation domain, and assaying the resultant constructs for interaction with Upf1p using the two-hybrid system. Fusions encoding either 237 or 477 amino acids from the amino-terminus of the original fragment demonstrated no detectable β-galactosidase activity. However, fusions encoding either 526 or 286 amino acids from the carboxyl-terminus of the original fragment did demonstrate detectable β-galactosidase activity. These results indicate that the acidic C-terminal domain of Nmd2p interacts with Upf1p.

The identification of Nmd2p as a Upf1p-interacting protein in a two-hybrid screen and the observation that disruption of the NMD2 gene yielded a nonsense-mediated mRNA decay phenotype equivalent to that obtained in strains harboring upf1 mutations suggests that Upf1p and Nmd2p interact with each other in vivo and that they perform different functions in the same decay pathway. This conclusion is strengthened by the finding that double mutants in which both the UPF1 and NMD2 gene products are functionally absent produce strains that have essentially identical phenotypes with regard to the half-lives of test mRNA transcripts such as CYH2 pre-mRNA. Thus, Upf1p and Nmd2p must function in closely related steps of the nonsense-mediated mRNA decay pathway.

A truncated form of Nmd2p was expressed in both the nucleus and cytoplasm and activity was functionally localized within the cell to the cytoplasm. The original GAL4 activation domain-NMD2 fusion plasmid encodes 764 amino acids of the C-terminal segment of Nmd2p (SEQ ID NO:4). Transcription of this GAL4-activation domain-NMD2 fusion was driven by a cryptic promoter in the ADH1 terminator present in the vector and the fusion protein was targeted to the nucleus by the SV40 T antigen nuclear localization signal (Chien, C-T. et al., (1991) supra. The 6.0 kb HindIII fragment encoding this fusion protein was also subcloned into pGAD2F so that transcription of the fusion protein was driven by the more potent ADH1 promoter. Since the SV40 T antigen nuclear localization signal (NLS) of the fusion protein is in a 36 bp EcoRI fragment (Benton, B. M. et al., (1990) Mol. Cell. Biol. 10:353–360, we also generated deletions of the NLS in the respective constructs. Plasmids expressing the different fusion proteins were transformed into the haploid strain HFY1200 which is wild-type for both UPF1 and NMD2. HFY1200 was derived from W303 by standard techniques (see, e.g., Rothstein, R. (1991) "Targeting, disruption, replacement, and allele rescue: integrative DNA transformation in yeast.", in *Methods in Enzymology* 194: *Guide to Yeast Genetics and Molecular Biology*, C. Guthrie and G. Fink, eds., Academic Press, pp. 281–301). Control experiments, using the two hybrid assay, showed that when NMD2 plasmids lacking the T antigen NLS were co-transformed with the original plasmid encoding the GAL4 DNA binding domain-UPF1 fusion no β-galactosidase activity was detectable, i.e., nuclear localization had been eliminated. Total RNA was isolated from transformants and Northern analysis was performed using a fragment of the CYH2 gene as a probe.

The Northern analysis results depicted in FIG. 5A show that a double mutant containing both upf1::URA3 and nmd2::HIS3 disruptions is phenotypically identical to either upf1 or nmd2 single mutants since the CYH2 pre-mRNA is stabilized in cells containing these disruptions. Total RNAs were isolated from each of the following strains: HFY3002 (UPF1/NMD2); HFY3005 (upf1Δ/NMD2); HFY3008 (UPF1/nma2Δ) and HFY3001 (upf1Δ/nmd2Δ) (see Table 2). RNAs were analyzed by Northern blotting using a radiolabeled CYH2 fragment as probe.

TABLE 2

Yeast Strains

| STRAIN | GENOTYPE |
|---|---|
| HFY1000 | MATa/MATα ade2-1/ade2-1 his3-11,15/his3-11,15 leu2-3,112/leu2-3,112 trp1-1/trp1-1 ura3-1/ura3-1 can1-100/can1-100 nmd2::HIS3/NMD2 |
| HFY1100 | MATα ade2-1 his3-11,15 leu2-3,112trp1-1 ura3-1 can1-100 NMD2 |
| HFY1200 | MATa ade2-1 his3-11,15 leu2-3,112 trp1-1 ura3-1 can1-100 NMD2 |
| HFY1300 | MATα ade2-1 his3-11,15 leu2-3,112 trp1-1 ura3-1 can1-100 nmd2::HIS3 |

TABLE 2-continued

Yeast Strains

| STRAIN | GENOTYPE |
|---|---|
| HFY1400 | MATa ade2-1 his3-11,15 leu2-3,112 trp1-1 ura3-1 can1-100 nmd2::HIS3 |
| HFY1201 | Same as HFY1200 but containing [pRIPPGKH2 (3) UAG] |
| HFY1202 | Same as HFY1200 but containing [pRIPPGKAsp UAG] |
| HFY1203 | Same as HFY1200 but containing [pRIPPGKH2 (2) UAG] |
| HFY1204 | Same as HFY1200 but containing [pRIPPGKH2 (1) UAG] |
| HFY1205 | Same as HFY1200 but containing [pRIPPGKXba UAG] |
| HFY1206 | Same as HFY1200 but containing [pRIPPGKBg1 UAG] |
| HFY1301 | Same as HFY1300 but containing [pRIPPGKH2 (3) UAG] |
| HFY1302 | Same as HFY1300 but containing [pRIPPGKAsp UAG] |
| HFY1303 | Same as HFY1300 but containing [pRIPPGKH2 (2) UAG] |
| HFY1304 | Same as HFY1300 but containing [pRIPPGKH2 (1) UAG] |
| HFY1305 | Same as HFY1300 but containing [pRIPPGKXba UAG] |
| HFY1306 | Same as HFY1300 but containing [pRIPPGKBg1 UAG] |
| HFY2000 | MATα ade2-1 his3-11,15 leu2-3,122 trp1-1 ura3-1 can1-100 rpb1-1 nmd2::HIS3 |
| HFY2106 | Same as HFY2000 but containing [pRS315] [pRIPPGKBg1 UAG] |
| HFY2206 | Same as HFY2000 but containing [pRS315-NMD2 (X-S)] [pRIPPGKBg1 UAG] |
| HFY3000 | MATα ade2-1 his3-11,15 leu2-3,112 trp1-1 ura3-1 can1-100 nmd2::HIS3 upf1::URA3 |
| HFY3001 | Same as HFY3000 but containing [pRS315] [pRS314] |
| HFY3002 | Same as HFY3000 but containing [pRS315-NMD2 (X-S)] [pRS314-UPF1] |
| HFY3005 | Same as HFY2000 but containing [pR315- NMD2 (X-S)] [pRS314] |
| HFY3008 | Same as HFY2000 but containing [pRS315] [pRS314-UPF1] |

The strains listed in Table 2 were prepared in this study. See Peltz, S. W. et al. (1993), supra, for a description of the "pRIPPGK__" plasmids listed above.

Overexpression of truncated Nmd2p in the cytoplasm results in a dominant-negative nonsense-mediated mRNA decay phenotype as shown in FIG. 5B. The yeast strain HFY1200 which is wild-type for both UPF1 and NMD2 was transformed with pGAD2F-NMD2-ADHt, pGAD2F-NMD2-ADHp, pGAD2F, pGAD2F-NMD2-ADHt- ΔNLS, pGAD2F-NMD2-ADNp-ΔNLS, respectively (see Table 3). Total RNA was isolated from these transformants and analyzed by Northern blotting using a CYH2 DNA fragment as probe. Lane 1 contained RNA isolated from HFY1300 (control); RNA in other lanes was from transformants of HFY1200 harboring the following plasmids; lane 2, pGAD2F-NMD2-ADHt ; lane 3, pGAD2F-NMD2-ADHp lane 4, pGAD2F; lane 5 pGAD2F-NMD2-ADHt-ΔNLS ; lane 6, pGAD2F-NMD2-ADHp-ΔNLS. Overexpression of truncated NMD2 fusion protein localized to the nucleus had no effect on the accumulation of the CYH2 pre-mRNA (FIG. 5B, lanes 2 and 3). Expression of the cytoplasmically localized fusion protein caused an accumulation of CYH2 pre-mRNA in a dosage dependent manner, i.e., expression of the fusion protein from the stronger promoter led to a greater accumulation of the CYH2 pre-mRNA than expression from the weaker promoter (FIG. 5B, lanes 5 and 6). This result establishes that over-expression of a truncated form of the Nmd2p C-terminus (i.e., containing up to 764 amino acids from the C-terminus (SEQ ID NO:4)) results in inhibition of the nonsense-mediated mRNA decay pathway. Shorter C-terminal fragments of Nmd2p are included in the invention as they are readily obtained by screening for inhibiting activity by the two-hybrid screening method coupled with analysis of heterologous transcript stability in the presence of overexpressed amounts of the fragment in the host strain.

TABLE 3

Plasmids

| PLASMIDS | RELEVANT YEAST SEQUENCES |
|---|---|
| pGAD2F | GAL4 activation domain-containing plasmid with 2μ and LEU2 selection markers (Chien, C.-T. et al. (1991) PNAS 88:9578–9582). |
| pGAD2F-NMD2-ADHp | 6.0-kb HindIII fragment from pGAD2-NMD2 replaced the 0.6-kb HindIII-HindIII fragment of pGAD2F such that the expression of the GAL4 activation domain -NMD2 fusion was driven by the ADH1 promoter. |
| pGAD2F-NMD2-ADHt | 6.0-kb HindIII fragment from pGAD2-NMD2 replaced the 0.6-kb HindIII-HindIII fragment of pGAD2F such that the expression of the GAL4 activation domain -NMD2 fusion was driven by the ADH1 terminator. |
| pGAD2F-NMD2-ADHp-ΔNLS | Same as pGAD2F-NMD2-ADHp except that the SV40 nuclear localization signal of the fusion protein was deleted. |
| pGAD2F-NMD2-ADHt-ΔNLS | Same as pGAD2F-NMD2-ADHt except that the SV40 nuclear localization signal of the fusion protein was deleted. |

EXAMPLE 6

Expression of NMD2 Antisense Transcript Inhibits the Nonsense-Mediate mRNA Decay Pathway Nonsense-mediated mRNA decay pathway function of a host cell (i.e., a prokaryotic or eukaryotic cell such as a yeast cell) is reduced or inhibited by providing within the cell a portion of the antisense strand of the NMD2 gene introduced into cells in which NMD2 is transcribed. The antisense oligonucleotide (either RNA or DNA) can be directly introduced into the cells in a form that is capable of binding to the NMD2 sense transcripts. Alternatively, a vector containing sequence which, once within the host cells, is transcribed into the appropriate antisense mRNA, can be the species administered to the cells. An antisense nucleic acid which hybridizes to the mRNA of the target gene can decrease or inhibit production of the polypeptide product encoded by the gene, by forming a double-stranded segment on the normally single-stranded mRNA transcript, and thereby interfering with translation.

A DNA sequence, such as a full or partial sequence of the NMD2 gene, is expressed as an antisense transcript. The sequence can be operably linked to appropriate expression control sequences and introduced into host cells by standard techniques well known to those of ordinary skill in the art. An effective amount of the expressed antisense transcript is produced such that translation of the NMD2 sense mRNA transcript is inhibited. By an equivalent method, UPF1 expression is inhibited by the introduction of UPF1 mRNA antisense transcript or a fragment thereof which binds to the UPF1 sense transcript, inhibiting translation and thereby, inhibiting the nonsense-mediated mRNA pathway. Antisense transcript production can be constitutive or controlled, as desired, according to the transcription regulatory sequences operably linked to the NMD2 or UPF1 DNA sequences for the production of antisense transcript.

Inhibition of the nonsense-mediated mRNA pathway using antisense transcripts to inhibit translation of a protein of the pathway (such as NMD2 or UPF1) is useful to enhance the stability of a nonsense codon-containing transcript which encodes a heterologous polypeptide to be produced in yeast cells or to enhance the production of a mutated endogenous polypeptide useful to the host cell or host organism.

EXAMPLE 7

Production of Heterologous Protein or Polypeptide in a Yeast Cell Inhibited in the Nonsense-Mediated mRNA Pathway A protein or polypeptide of interest is produced by providing an expression vector encoding a gene for a heterologous protein. The expressed transcript of the gene encodes a nonsense codon in a transcript destabilizing 5' portion of the transcript such that the transcript is at least 2 fold less stable in a wild-type strain than in a nonsense-mediated mRNA decay-inhibited host strain. Nonsense-mediated mRNA decay is inhibited by 1) mutating the NMD2 gene such that no functional Nmd2p is produced 2) overexpressing a C-terminal fragment of Nmd2p such that the fragment binds to Upf1p inhibiting its function; or 3) expressing sufficient NMD2 or UPF1 antisense transcript to hybridize to NMD2 or UPF1 sense transcript preventing its translation into functional Nmd2p or Upf1p, respectively. All of these methods can be carried out by standard procedures.

If it is desired that an amino acid be substituted at the nonsense codon position, then the host strain used is also an amino acid substitution suppressor strain. The suppressor strain is chosen such that a specific amino acid (dictated by the type of suppressor mutation in the host strain) is substituted at the nonsense codon. The substituted amino acid can be an amino acid encoded by the natural codon at that site. The substituted amino acid can be different from the naturally encoded amino acid if it is desired to test the affect of that amino acid on the conformation or activity of the encoded protein.

If the heterologous protein to be expressed is toxic to the host cell, inhibition of the nonsense-mediated mRNA decay pathway can be controlled by the inducible expression of, for example, Nmd2p C-terminal fragment or NMD2 antisense transcript. Controllable inhibition of the decay pathway allows transcript stabilization and translation at a point in the host yeast cell culture growth such that maximum production of the toxic protein occurs prior to the death of the host cells.

Following inhibition of the nonsense-mediated mRNA pathway and translation of the stabilized nonsense codon-containing transcript into the desired heterologous protein or protein fragment is isolated from the yeast host cells by standard protein purification methods.

EXAMPLE 8

Production of Antibody to Nmd2p or a C-terminal Fragment of Nmd2p

Nmd2p or Nmd2p C-terminal fragment polypeptide of the invention can be produced by first transforming a suitable host cell with the entire NMD2 gene (for the production of Nmd2p) or with a partial NMD2 sequence (encoding the C-terminal part of Nmd2p), respectively, cloned into a suitable expression vehicle followed by expression of the desired protein or polypeptide.

Those of ordinary skill in the field of molecular biology will understand that any of a wide variety of expression systems can be used to provide the protein or polypeptide. The precise host cell used is not critical to the invention. The polypeptide can be produced in a prokaryotic host (e.g. *E. coli*) or in a eukaryotic host (e.g., *Saccharomyces cerevisiae*). The method of transformation of the cells and the choice of expression vehicle will depend on the host system selected. Methods described herein provide sufficient guidance to successfully carry out the production, purification and identification of Nmd2p or the Nmd2p C-terminal fragment.

Once the Nmd2p or Nmd2p C-terminal fragment (or fragment or analog thereof) is expressed, it is isolated, e.g., using immunoaffinity chromatography. In one example, an anti-Nmd2p or anti-(Nmd2p C-terminal fragment) antibody can be attached to a column and used to isolate Nmd2p or Nmd2p C-terminal fragment, respectively. Lysis and fractionation of Nmd2p or Nmd2p C-terminal fragment-containing host cells prior to affinity chromatography can be performed by standard methods. Once isolated, the recombinant protein can, if desired, be further purified, e.g., by high performance liquid chromatography (see, e.g., Fisher, *Laboratory Techniques In Biochemistry and Molecular Biology*, eds., Work and Burdon, Elsevier, (1980)).

Nmd2p or fragments thereof, particularly short fragments which inhibit the nonsense-mediated mRNA decay pathway, can also be produced by chemical synthesis by standard solution or solid phase peptide synthesis techniques.

Substantially pure Nmd2p or Nmd2p C-terminal fragment can be used to raise antibodies. The antibodies are useful for screening, by Western blot analysis, host strains overexpressing Nmd2p or Nmd2p C-terminal fragment, thereby identifying candidate strains which produce a desired amount of Nmd2p or Nmd2p C-terminal fragment.

Antibodies directed to the polypeptide of interest, Nmd2p or Nmd2p C-terminal fragment, are produced as follows. Peptides corresponding to all or part of the polypeptide of interest are produced using a peptide synthesizer by standard techniques, or are isolated and purified as described above. The peptides are coupled to KLH with m-maleimide benzoic acid N-hydroxysuccinimide ester. The KLH-peptide is mixed with Freund's adjuvant and injected into animals, e.g. guinea pigs or goats, to produce polyclonal antibodies.

Monoclonal antibodies can be prepared using the polypeptide of interest described above and standard hybridoma technology (see, e.g., Kohler et al., Nature (1975) 256:495; Kohler et al., Eur. J. Immunol. (1976) 6:292; Kohler et al., Eur. J. Immunol. (1976) 6:511; Hammerling et al., in *Monoclonal Antibodies and T Cell Hybridomas*, Elsevier, N.Y., (1981), which are incorporated herein by reference). Antibodies are purified by peptide antigen affinity chromatography.

Once produced, antibodies are tested for specific Nmd2p or Nmd2p C-terminal fragment binding by Western blot or immunoprecipitation analysis by standard techniques.

USE

Overexpressing the C-terminal truncated form of Nmd2p in a cell (such as a yeast cell) provides for the inhibition of the nonsense-mediated mRNA decay pathway. Disruption or mutation of the NMD2 gene or NMD2 antisense transcript expression are another methods for inhibiting the nonsense-mediated mRNA decay pathway. As a result, a transcript for a heterologous protein which contains at least one stop codon within a transcript-destabilizing 5' portion will be specifically stabilized when expressed in a host cell inhibited in a nonsense-mediated mRNA decay pathway. Such stabilization allows translation of the stabilized transcript in a yeast suppressor mutant to produce a full length peptide with an amino acid inserted at the position of the nonsense codon. The inserted amino acid is specific to the suppressor mutant host in which the heterologous gene and the Nmd2p C-terminus are expressed. The relevant properties of each of the mutant heterologous proteins are compared to the properties of the wild-type protein, and altered heterologous proteins having desired properties are collected. Such properties may include but are not limited to protein receptor binding, antibody binding, enzymatic activity, three dimensional structure, and other biological and physical properties known to those of ordinary skill in the arts of biochemistry and protein chemistry.

The invention is also useful in the production of heterologous protein fragments by inserting into the DNA a stop codon within a transcript-destabilizing 5' portion of the coding sequence at a site at which translation is to stop thereby producing an N-terminal protein fragment. Fragments useful in pharmaceutical or other applications can be isolated in large quantities if so desired by techniques well known to those of ordinary skill in the art.

Those of ordinary skill in the art will recognize, or be able to ascertain, using no more than routine experimentation, many equivalents to the specific embodiments of the invention described herein. These and all other such equivalents are intended to be encompassed by the following claims.

What is claimed is:

1. A substantially pure DNA consisting of the sequence of SEQ ID NO:1.

2. A vector comprising the DNA of claim 1 operably linked to a transcriptional regulatory sequence.

3. A recombinant cell which comprises the DNA of claim 1, wherein said cell is a yeast, bacterial, or isolated mammalian cell.

4. A recombinant cell which comprises the vector of claim 2, wherein said cell is a yeast, bacterial, or isolated mammalian cell.

5. A substantially pure DNA consisting of the nucleotide sequence of SEQ ID NO:3.

6. A vector comprising the DNA of claim 5 operably linked to a transcriptional regulatory sequence.

7. A vector of claim 6, wherein said transcription is controllable.

8. A recombinant cell which comprises the DNA of claim 5, wherein said cell is a yeast, bacterial, or isolated mammalian cell.

9. A recombinant cell which comprises the vector of claim 6, wherein said cell is a yeast, bacterial, or isolated mammalian cell.

10. A recombinant cell which comprises the vector of claim 9, wherein said cell is a yeast, bacterial, or isolated mammalian cell.

11. A substantially pure nucleic acid which encodes the amino acid sequence of SEQ ID NO:2.

12. A vector comprising the nucleic acid of claim 11 operably linked to a transcriptional regulatory sequence.

13. A substantially pure nucleic acid which encodes the amino acid sequence of SEQ ID NO:4.

14. A vector comprising the nucleic acid of claim 13 operably linked to a transcriptional regulatory sequence.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 4080 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
CCTGAATGAC CTTTATCTTA ATTATGCACC ATCATATAGC GTTTCTATGA TCACTACGGG      60

ATATTATGAT ATTGTTAGGG GGTTATATTG AATATTTCTT AGGGCATGAG GATGATATTA     120

GGGTTATTAA TAGGTTTACA ATTATATAAT TTATGTGATA ATTATCACTT GATACGAATT     180

GATGGAGCCT GCTTCTTTTT TTTTTTTTCA CTTTCTTGGC AGTCACTGAA AAACTGCATT     240

CGAATACAGG TTTGAGAAAC TAATGAGGCC CATATTACTT TACAATGAAC AGTAACAATC     300

AACTTAAATG CTTAAATAAT CTAATATTGT ATCTGCATTG ATAATACATT GGACAGAAAT     360

TATGGACGTA TGTTTGATTT ATCTTACTGT GGCCAGATCG GCCTTTCAGT ACTTCTAAGG     420

TTTTATACTA ACTTCTTTTA TTGATCGTTG TAAACTACGG TAACAATTAT GTATCAACAG     480

GATGGACGGA AAAAGAATT GCATGATTTG AACACCCGAG CTTGGAATGG CGAAGAAGTC      540

TTTCCCCTGA AAAGTAAAAA ACTGGATTCC AGTATAAAGA GAAACACTGG CTTTATAAAA     600

AAACTAAAGA AGGGTTTTGT GAAAGGTTCA GAATCTTCAT TATTGAAAGA TTTAAGTGAG     660

GCGTCCTTGG AAAAGTACCT ATCAGAGATA ATAGTGACGG TAACAGAATG TCTGCTAAAT     720

GTTTTGAATA AAAATGATGA CGTAATTGCC GCTGTTGAGA TCATAAGTGG ACTTCATCAA     780

AGGTTCAATG GCCGATTTAC TAGTCCGCTT TTAGGAGCTT TTTTACAAGC TTTTGAGAAC     840

CCCTCTGTTG ACATTGAATC CGAAAGAGAT GAGCTTCAAA GGATAACCAG AGTTAAAGGT     900

AATCTTCGGG TATTTACCGA GCTTTATTTA GTTGGAGTTT TTAGAACATT GGATGATATT     960

GAGTCGAAAG ATGCTATTCC AAACTTCCTA CAGAAGAAAA CTGGGCGAAA GGATCCGTTG    1020

TTATTCAGTA TTCTCAGAGA GATTCTTAAT TATAAGTTCA AATTGGGCTT TACTACCACT    1080

ATTGCGACCG CATTTATTAA GAAATTTGCA CCTTTGTTTC GCGACGATGA TAATTCTTGG    1140

GATGATTTAA TATATGACTC GAAGTTAAAA GGTGCGTTAC AGTCTCTGTT TAAGAATTTT    1200

ATAGACGCCA CTTTTGCGAG GGCCACAGAA CTGCATAAGA AGGTCAATAA ACTGCAAAGA    1260

GAACATCAGA AATGCCAAAT AAGAACGGGA AAATTGAGAG ATGAGTACGT AGAGGAGTAC    1320

GACAAGTTAC TTCCAATATT CATTAGGTTC AAGACATCTG CAATTACTTT GGGAGAATTT    1380
```

-continued

| | | | | | |
|---|---|---|---|---|---|
| TTTAAGTTAG | AAATTCCGGA | GCTTGAAGGT | GCCTCTAATG | ATGATCTGAA | AGAAACAGCT | 1440 |
| TCTCCAATGA | TCACGAATCA | GATATTGCCA | CCCAACCAAC | GATTATGGGA | AAATGAAGAT | 1500 |
| ACAAGGAAAT | TTTATGAAAT | CTTACCAGAT | ATCTCAAAAA | CAGTAGAAGA | ATCACAATCT | 1560 |
| TCTAAAACAG | AAAAGATTC | AAACGTTAAC | TCAAAAAATA | TCAATCTATT | CTTTACGGAT | 1620 |
| TTGGAAATGG | CAGATTGTAA | AGATATAATC | GATGACCTTT | CAAATAGATA | TTGGTCATCA | 1680 |
| TATTTGGACA | ACAAAGCCAC | AAGAAATCGA | ATATTGAAAT | TTTTCATGGA | ACACAAGAT | 1740 |
| TGGAGCAAAC | TGCCAGTGTA | TTCCAGATTT | ATTGCAACAA | ATAGCAAATA | TATGCCGGAA | 1800 |
| ATTGTTTCTG | AGTTTATTAA | CTACCTAGAC | AATGGCTTCA | GGAGTCAATT | ACATTCTAAT | 1860 |
| AAGATTAACG | TTAAAACAT | CATCTTCTTC | AGTGAAATGA | TTAAATTTCA | ATTAATACCA | 1920 |
| TCGTTTATGA | TTTTCATAA | GATTAGAACA | TTAATCATGT | ATATGCAAGT | TCCAAATAAC | 1980 |
| GTAGAAATTT | TGACGGTTTT | GTTGGAGCAC | TCAGGGAAAT | TTCTGCTAAA | TAAGCCAGAA | 2040 |
| TATAAGGAAT | TAATGGAAAA | AATGGTCCAA | CTAATCAAGG | ATAAAAAAA | TGATAGGCAA | 2100 |
| TTGAACATGA | ACATGAAAAG | CGCCTTAGAA | AACATAATTA | CTTTACTTTA | TCCCCCTTCT | 2160 |
| GTAAAATCAT | TAAATGTTAC | GGTAAAAACA | ATAACGCCTG | AACAACAGTT | TTATCGCATA | 2220 |
| TTAATTAGAA | GTGAACTAAG | TAGCCTAGAC | TTCAAACACA | TTGTCAAGTT | GGTTCGGAAA | 2280 |
| GCTCACTGGG | ACGATGTAGC | TATTCAGAAA | GTGCTGTTTT | CTCTGTTTTC | AAAACCACAT | 2340 |
| AAGATTAGCT | ATCAAAATAT | TCCTTATTA | ACAAAGTTC | TAGGCGGTCT | ATACAGTTAC | 2400 |
| CGCCGCGATT | TCGTCATCAG | ATGTATAGAC | CAAGTACTGG | AAAACATTGA | GCGAGGCTTA | 2460 |
| GAAATTAACG | ATTATGGACA | AACATGCAT | AGAATATCAA | ATGTCAGATA | CTTAACTGAA | 2520 |
| ATATTCAACT | TTGAAATGAT | AAAATCCGAT | GTTTGTTAG | ATACTATCTA | CCACATTATT | 2580 |
| CGGTTTGGTC | ATATCAACAA | TCAACCCAAT | CCATTTATT | TAAACTACTC | AGATCCACCG | 2640 |
| GATAATTATT | TCAGGATTCA | ACTAGTCACT | ACAATTCTGT | TAAATATCAA | CAGGACCCCT | 2700 |
| GCAGCTTTTA | CTAAGAAATG | CAAACTTTTG | CTGAGGTTTT | TCGAGTATTA | TACTTTATT | 2760 |
| AAAGAACAAC | CTTTACCCAA | GGAAACAGAA | TTCAGAGTTT | CAAGCACATT | TAAAAAATAT | 2820 |
| GAGAATATTT | TCGGAAACAC | TAAATTTGAA | AGGTCAGAAA | ATTTGGTAGA | AAGTGCCTCA | 2880 |
| AGGTTGGAAA | GTTACTGAA | ATCATTAAAC | GCAATAAAAA | GTAAAGACGA | CAGAGTGAAG | 2940 |
| GGATCTTCTG | CAAGCATTCA | CAACGGTAAG | GAGAGTGCTG | TTCCTATCGA | GTCAATCACC | 3000 |
| GAAGATGATG | AGGATGAAGA | TGATGAAAAC | GACGATGGTG | TCGATTACT | AGGAGAAGAT | 3060 |
| GAAGACGCGG | AGATAAGTAC | ACCGAACACA | GAGTCAGCGC | CAGGAAAACA | TCAGGCAAAG | 3120 |
| CAAGACGAAA | GTGAAGATGA | AGACGATGAG | GACGATGACG | AGGATGATGA | CGATGACGAT | 3180 |
| GACGATGATG | ATGATGATGG | AGAAGAAGGC | GATGAGGATG | ATGATGAAGA | TGATGATGAT | 3240 |
| GAGGATGATG | ATGATGAAGA | AGAAGAAGAC | AGCGACTCTG | ATTTGGAGTA | TGGTGGTGAT | 3300 |
| CTTGACGCAG | ACAGAGATAT | TGAAATGAAA | CGAATGTATG | AAGAGTACGA | GAGAAAACTA | 3360 |
| AAGGATGAGG | AAGAAAGGAA | AGCGGAAGAA | GAATTGGAAA | GGCAATTTCA | GAAAATGATG | 3420 |
| CAAGAATCCA | TAGACGCAAG | GAAAAGCGAA | AAGGTTGTTG | CCAGTAAAAT | TCCAGTAATT | 3480 |
| TCGAAGCCAG | TCAGCGTTCA | AAAACCTTTA | TTATTAAAAA | AGAGTGAAGA | ACCTTCTTCA | 3540 |
| AGCAAGGAGA | CCTACGAAGA | GTTATCCAAG | CCAAAGAAGA | TTGCATTTAC | GTTCTTGACT | 3600 |
| AAAAGCGGTA | AGAAGACACA | ATCAAGAATT | TTACAATTAC | CAACGGATGT | GAAATTTGTC | 3660 |
| TCTGATGTCC | TTGAAGAAGA | AGAGAAACTA | AAAACCGAGC | GAAACAAGAT | TAAAAAGATT | 3720 |
| GTTTTAAAAC | GTTCTTTCGA | CTGAGATTCT | TTGCGAATAT | AGTTCTTTAA | ATTTTTACTA | 3780 |

-continued

```
TATATGCCCA CTTATGTTTG GCTCTATTAA ATGGCTACGT GTTTATATAG TACCGTTTAT  3840

GACGCTGTAT TTTTATTTAC ACTGCTTTCC AGGAGATTAA AGAGCGGAGT GTTAGTCAAC  3900

TCTCACGACA ACAACAGTTA TATCGTCTTC TTTACCACCG CTGTAGTTTT TGCCAGTTAG  3960

CTTAGAAATC TCTTGCGCAA AAACACTGGG GTAATTGGGG TCCTTGCTTA AACTGACAAC  4020

ATTGTCCACA AACTTCTGGG ATAATAGCTG TAACTCATCG TTTGTTCTCG CAGCGTTATC  4080
```

( 2 ) INFORMATION FOR SEQ ID NO:2:

( i ) SEQUENCE CHARACTERISTICS:
        ( A ) LENGTH: 1089 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:2:

```
Met Asp Asp Gly Arg Lys Lys Glu Leu His Asp Leu Asn Thr Arg Ala
 1               5                  10                  15

Trp Asn Gly Glu Val Phe Pro Leu Lys Ser Lys Lys Leu Asp Ser
            20                  25                  30

Ser Ile Lys Arg Asn Thr Gly Phe Ile Lys Lys Leu Lys Lys Gly Phe
        35                  40                  45

Val Lys Gly Ser Glu Ser Ser Leu Leu Lys Asp Leu Ser Glu Ala Ser
50                  55                  60

Leu Glu Lys Tyr Leu Ser Glu Ile Ile Val Thr Val Thr Glu Cys Leu
65                  70                  75                  80

Leu Asn Val Leu Asn Lys Asn Asp Asp Val Ile Ala Ala Val Glu Ile
                85                  90                  95

Ile Ser Gly Leu His Gln Arg Phe Asn Gly Arg Phe Thr Ser Pro Leu
            100                 105                 110

Leu Gly Ala Phe Leu Gln Ala Phe Glu Asn Pro Ser Val Asp Ile Glu
        115                 120                 125

Ser Glu Arg Asp Glu Leu Gln Arg Ile Thr Arg Val Lys Gly Asn Leu
    130                 135                 140

Arg Val Phe Thr Glu Leu Tyr Leu Val Gly Val Phe Arg Thr Leu Asp
145                 150                 155                 160

Asp Ile Glu Ser Lys Asp Ala Ile Pro Asn Phe Leu Gln Lys Lys Thr
                165                 170                 175

Gly Arg Lys Asp Pro Leu Leu Phe Ser Ile Leu Arg Glu Ile Leu Asn
            180                 185                 190

Tyr Lys Phe Lys Leu Gly Phe Thr Thr Ile Ala Thr Ala Phe Ile
        195                 200                 205

Lys Lys Phe Ala Pro Leu Phe Arg Asp Asp Asp Asn Ser Trp Asp Asp
    210                 215                 220

Leu Ile Tyr Asp Ser Lys Leu Lys Gly Ala Leu Gln Ser Leu Phe Lys
225                 230                 235                 240

Asn Phe Ile Asp Ala Thr Phe Ala Arg Ala Thr Glu Leu His Lys Lys
                245                 250                 255

Val Asn Lys Leu Gln Arg Glu His Gln Lys Cys Gln Ile Arg Thr Gly
            260                 265                 270

Lys Leu Arg Asp Glu Tyr Val Glu Glu Tyr Asp Lys Leu Leu Pro Ile
        275                 280                 285

Phe Ile Arg Phe Lys Thr Ser Ala Ile Thr Leu Gly Glu Phe Phe Lys
    290                 295                 300
```

```
Leu  Glu  Ile  Pro  Glu  Leu  Gly  Ala  Ser  Asn  Asp  Asp  Leu  Lys  Glu
305            310                 315                           320

Thr  Ala  Ser  Pro  Met  Ile  Thr  Asn  Gln  Ile  Leu  Pro  Pro  Asn  Gln  Arg
                    325                 330                           335

Leu  Trp  Glu  Asn  Glu  Asp  Thr  Arg  Lys  Phe  Tyr  Glu  Ile  Leu  Pro  Asp
               340                 345                           350

Ile  Ser  Lys  Thr  Val  Glu  Glu  Ser  Gln  Ser  Ser  Lys  Thr  Glu  Lys  Asp
          355                 360                           365

Ser  Asn  Val  Asn  Ser  Lys  Asn  Ile  Asn  Leu  Phe  Phe  Thr  Asp  Leu  Glu
          370                 375                           380

Met  Ala  Asp  Cys  Lys  Asp  Ile  Ile  Asp  Asp  Leu  Ser  Asn  Arg  Tyr  Trp
385                      390                 395                           400

Ser  Ser  Tyr  Leu  Asp  Asn  Lys  Ala  Thr  Arg  Asn  Arg  Ile  Leu  Lys  Phe
                    405                 410                           415

Phe  Met  Glu  Thr  Gln  Asp  Trp  Ser  Lys  Leu  Pro  Val  Tyr  Ser  Arg  Phe
               420                 425                           430

Ile  Ala  Thr  Asn  Ser  Lys  Tyr  Met  Pro  Glu  Ile  Val  Ser  Glu  Phe  Ile
          435                 440                           445

Asn  Tyr  Leu  Asp  Asn  Gly  Phe  Arg  Ser  Gln  Leu  His  Ser  Asn  Lys  Ile
     450                 455                      460

Asn  Val  Lys  Asn  Ile  Ile  Phe  Phe  Ser  Glu  Met  Ile  Lys  Phe  Gln  Leu
465                      470                 475                           480

Ile  Pro  Ser  Phe  Met  Ile  Phe  His  Lys  Ile  Arg  Thr  Leu  Ile  Met  Tyr
                    485                 490                           495

Met  Gln  Val  Pro  Asn  Asn  Val  Glu  Ile  Leu  Thr  Val  Leu  Leu  Glu  His
               500                 505                           510

Ser  Gly  Lys  Phe  Leu  Leu  Asn  Lys  Pro  Glu  Tyr  Lys  Glu  Leu  Met  Glu
          515                 520                           525

Lys  Met  Val  Gln  Leu  Ile  Lys  Asp  Lys  Lys  Asn  Asp  Arg  Gln  Leu  Asn
     530                 535                           540

Met  Asn  Met  Lys  Ser  Ala  Leu  Glu  Asn  Ile  Ile  Thr  Leu  Leu  Tyr  Pro
545                      550                 555                           560

Pro  Ser  Val  Lys  Ser  Leu  Asn  Val  Thr  Val  Lys  Thr  Ile  Thr  Pro  Glu
                    565                 570                           575

Gln  Gln  Phe  Tyr  Arg  Ile  Leu  Ile  Arg  Ser  Glu  Leu  Ser  Ser  Leu  Asp
               580                 585                           590

Phe  Lys  His  Ile  Val  Lys  Leu  Val  Arg  Lys  Ala  His  Trp  Asp  Asp  Val
          595                 600                           605

Ala  Ile  Gln  Lys  Val  Leu  Phe  Ser  Leu  Phe  Ser  Lys  Pro  His  Lys  Ile
     610                 615                      620

Ser  Tyr  Gln  Asn  Ile  Pro  Leu  Leu  Thr  Lys  Val  Leu  Gly  Gly  Leu  Tyr
625                      630                 635                           640

Ser  Tyr  Arg  Arg  Asp  Phe  Val  Ile  Arg  Cys  Ile  Asp  Gln  Val  Leu  Glu
                    645                 650                           655

Asn  Ile  Glu  Arg  Gly  Leu  Glu  Ile  Asn  Asp  Tyr  Gly  Gln  Asn  Met  His
               660                 665                           670

Arg  Ile  Ser  Asn  Val  Arg  Tyr  Leu  Thr  Glu  Ile  Phe  Asn  Phe  Glu  Met
          675                 680                      685

Ile  Lys  Ser  Asp  Val  Leu  Leu  Asp  Thr  Ile  Tyr  His  Ile  Ile  Arg  Phe
     690                 695                      700

Gly  His  Ile  Asn  Asn  Gln  Pro  Asn  Pro  Phe  Tyr  Leu  Asn  Tyr  Ser  Asp
705                      710                 715                           720

Pro  Pro  Asp  Asn  Tyr  Phe  Arg  Ile  Gln  Leu  Val  Thr  Thr  Ile  Leu  Leu
                    725                 730                           735
```

Asn Ile Asn Arg Thr Pro Ala Ala Phe Thr Lys Lys Cys Lys Leu Leu
            740                 745                 750

Leu Arg Phe Phe Glu Tyr Tyr Thr Phe Ile Lys Glu Gln Pro Leu Pro
        755                 760                 765

Lys Glu Thr Glu Phe Arg Val Ser Ser Thr Phe Lys Lys Tyr Glu Asn
770                     775                 780

Ile Phe Gly Asn Thr Lys Phe Glu Arg Ser Glu Asn Leu Val Glu Ser
785                 790                 795                 800

Ala Ser Arg Leu Glu Ser Leu Leu Lys Ser Leu Asn Ala Ile Lys Ser
                805                 810                 815

Lys Asp Asp Arg Val Lys Gly Ser Ser Ala Ser Ile His Asn Gly Lys
            820                 825                 830

Glu Ser Ala Val Pro Ile Glu Ser Ile Thr Glu Asp Asp Glu Asp Glu
            835                 840                 845

Asp Asp Glu Asn Asp Asp Gly Val Asp Leu Leu Gly Glu Asp Glu Asp
        850                 855                 860

Ala Glu Ile Ser Thr Pro Asn Thr Glu Ser Ala Pro Gly Lys His Gln
865                 870                 875                 880

Ala Lys Gln Asp Glu Ser Glu Asp Glu Asp Asp Glu Asp Asp Asp Glu
                885                 890                 895

Asp Asp Asp Asp Asp Asp Asp Asp Asp Asp Asp Gly Glu Glu Gly
            900                 905                 910

Asp Glu Asp Asp Asp Glu Asp Asp Asp Glu Asp Asp Asp Asp Glu
            915                 920                 925

Glu Glu Glu Asp Ser Asp Ser Asp Leu Glu Tyr Gly Gly Asp Leu Asp
930                 935                 940

Ala Asp Arg Asp Ile Glu Met Lys Arg Met Tyr Glu Glu Tyr Glu Arg
945                 950                 955                 960

Lys Leu Lys Asp Glu Glu Glu Arg Lys Ala Glu Glu Glu Leu Glu Arg
                965                 970                 975

Gln Phe Gln Lys Met Met Gln Glu Ser Ile Asp Ala Arg Lys Ser Glu
            980                 985                 990

Lys Val Val Ala Ser Lys Ile Pro Val Ile Ser Lys Pro Val Ser Val
        995                 1000                1005

Gln Lys Pro Leu Leu Leu Lys Lys Ser Glu Glu Pro Ser Ser Ser Lys
1010                    1015                1020

Glu Thr Tyr Glu Glu Leu Ser Lys Pro Lys Lys Ile Ala Phe Thr Phe
1025                1030                1035                1040

Leu Thr Lys Ser Gly Lys Lys Thr Gln Ser Arg Ile Leu Gln Leu Pro
                1045                1050                1055

Thr Asp Val Lys Phe Val Ser Asp Val Leu Glu Glu Glu Glu Lys Leu
            1060                1065                1070

Lys Thr Glu Arg Asn Lys Ile Lys Lys Ile Val Leu Lys Arg Ser Phe
            1075                1080                1085

Asp (2) INFORMATION FOR SEQ ID NO:3:

(i) SEQUENCE CHARACTERISTICS:
        (A) LENGTH: 2295 base pairs
        (B) TYPE: nucleic acid
        (C) STRANDEDNESS: single
        (D) TOPOLOGY: linear (ii) MOLECULE TYPE: DNA -continued (x i) SEQUENCE DESCRIPTION: SEQ ID NO:3:

```
ATCACGAATC AGATATTGCC ACCCAACCAA CGATTATGGG AAAATGAAGA TACAAGGAAA    60
TTTTATGAAA TCTTACCAGA TATCTCAAAA ACAGTAGAAG AATCACAATC TTCTAAAACA   120
GAAAAAGATT CAAACGTTAA CTCAAAAAAT ATCAATCTAT TCTTTACGGA TTTGGAAATG   180
GCAGATTGTA AAGATATAAT CGATGACCTT TCAAATAGAT ATTGGTCATC ATATTTGGAC   240
AACAAAGCCA CAAGAAATCG AATATTGAAA TTTTTCATGG AAACACAAGA TTGGAGCAAA   300
CTGCCAGTGT ATTCCAGATT TATTGCAACA AATAGCAAAT ATATGCCGGA AATTGTTTCT   360
GAGTTTATTA ACTACCTAGA CAATGGCTTC AGGAGTCAAT TACATTCTAA TAAGATTAAC   420
GTTAAAAACA TCATCTTCTT CAGTGAAATG ATTAAATTTC AATTAATACC ATCGTTTATG   480
ATTTTTCATA AGATTAGAAC ATTAATCATG TATATGCAAG TTCCAAATAA CGTAGAAATT   540
TTGACGGTTT TGTTGGAGCA CTCAGGGAAA TTTCTGCTAA ATAAGCCAGA ATATAAGGAA   600
TTAATGGAAA AAATGGTCCA ACTAATCAAG GATAAAAAAA ATGATAGGCA ATTGAACATG   660
AACATGAAAA GCGCCTTAGA AAACATAATT ACTTACTTT ATCCCCTTC TGTAAAATCA   720
TTAAATGTTA CGGTAAAAAC AATAACGCCT GAACAACAGT TTATCGCAT ATTAATTAGA   780
AGTGAACTAA GTAGCCTAGA CTTCAAACAC ATTGTCAAGT TGGTTCGGAA AGCTCACTGG   840
GACGATGTAG CTATTCAGAA AGTGCTGTTT TCTCTGTTTT CAAAACCACA TAAGATTAGC   900
TATCAAAATA TTCCCTTATT AACAAAAGTT CTAGGCGGTC TATACAGTTA CCGCCGCGAT   960
TTCGTCATCA GATGTATAGA CCAAGTACTG GAAAACATTG AGCGAGGCTT AGAAATTAAC  1020
GATTATGGAC AAAAACATGCA TAGAATATCA AATGTCAGAT ACTTAACTGA AATATTCAAC  1080
TTTGAAATGA TAAAATCCGA TGTTTTGTTA GATACTATCT ACCACATTAT TCGGTTTGGT  1140
CATATCAACA ATCAACCCAA TCCATTTTAT TTAAACTACT CAGATCCACC GGATAATTAT  1200
TTCAGGATTC AACTAGTCAC TACAATTCTG TTAAATATCA ACAGGACCCC TGCAGCTTTT  1260
ACTAAGAAAT GCAAACTTTT GCTGAGGTTT TTCGAGTATT ATACTTTTAT TAAAGAACAA  1320
CCTTTACCCA AGGAAACAGA ATTCAGAGTT TCAAGCACAT TTAAAAAATA TGAGAATATT  1380
TTCGGAAACA CTAAATTTGA AAGGTCAGAA AATTTGGTAG AAAGTGCCTC AAGGTTGGAA  1440
AGTTTACTGA AATCATTAAA CGCAATAAAA AGTAAAGACG ACAGAGTGAA GGGATCTTCT  1500
GCAAGCATTC ACAACGGTAA GGAGAGTGCT GTTCCTATCG AGTCAATCAC CGAAGATGAT  1560
GAGGATGAAG ATGATGAAAA CGACGATGGT GTCGATTTAC TAGGAGAAGA TGAAGACGCG  1620
GAGATAAGTA CACCGAACAC AGAGTCAGCG CCAGGAAAAC ATCAGGCAAA GCAAGACGAA  1680
AGTGAAGATG AAGACGATGA GGACGATGAC GAGGATGATG ACGATGACGA TGACGATGAT  1740
GATGATGATG GAGAAGAAGG CGATGAGGAT GATGATGAAG ATGATGATGA TGAGGATGAT  1800
GATGATGAAG AAGAAGAAGA CAGCGACTCT GATTTGGAGT ATGGTGGTGA TCTTGACGCA  1860
GACAGAGATA TTGAAATGAA ACGAATGTAT GAAGAGTACG AGAGAAAACT AAAGGATGAG  1920
GAAGAAAGGA AAGCGGAAGA AGAATTGGAA AGGCAATTTC AGAAAATGAT GCAAGAATCC  1980
ATAGACGCAA GGAAAAGCGA AAAGGTTGTT GCCAGTAAAA TTCCAGTAAT TTCGAAGCCA  2040
GTCAGCGTTC AAAAACCTTT ATTATTAAAA AAGAGTGAAG AACCTTCTTC AAGCAAGGAG  2100
ACCTACGAAG AGTTATCCAA GCCAAGAAG ATTGCATTTA CGTTCTTGAC TAAAAGCGGT  2160
AAGAAGACAC AATCAAGAAT TTACAATTA CCAACGGATG TGAAATTTGT CTCTGATGTC  2220
CTTGAAGAAG AAGAGAAACT AAAAACCGAG CGAAACAAGA TTAAAAAGAT TGTTTTAAAA  2280
CGTTCTTTCG ACTGA                                                  2295
```

( 2 ) INFORMATION FOR SEQ ID NO:4:

( i ) SEQUENCE CHARACTERISTICS:
        ( A ) LENGTH: 764 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Ile  Thr  Asn  Gln  Ile  Leu  Pro  Pro  Asn  Gln  Arg  Leu  Trp  Glu  Asn  Glu
  1                  5                   10                            15

Asp  Thr  Arg  Lys  Phe  Tyr  Glu  Ile  Leu  Pro  Asp  Ile  Ser  Lys  Thr  Val
                20                   25                       30

Glu  Glu  Ser  Gln  Ser  Ser  Lys  Thr  Glu  Lys  Asp  Ser  Asn  Val  Asn  Ser
            35                    40                      45

Lys  Asn  Ile  Asn  Leu  Phe  Phe  Thr  Asp  Leu  Glu  Met  Ala  Asp  Cys  Lys
       50                   55                       60

Asp  Ile  Ile  Asp  Asp  Leu  Ser  Asn  Arg  Tyr  Trp  Ser  Ser  Tyr  Leu  Asp
 65                       70                    75                            80

Asn  Lys  Ala  Thr  Arg  Asn  Arg  Ile  Leu  Lys  Phe  Phe  Met  Glu  Thr  Gln
                 85                        90                       95

Asp  Trp  Ser  Lys  Leu  Pro  Val  Tyr  Ser  Arg  Phe  Ile  Ala  Thr  Asn  Ser
                100                  105                       110

Lys  Tyr  Met  Pro  Glu  Ile  Val  Ser  Glu  Phe  Ile  Asn  Tyr  Leu  Asp  Asn
            115                   120                        125

Gly  Phe  Arg  Ser  Gln  Leu  His  Ser  Asn  Lys  Ile  Asn  Val  Lys  Asn  Ile
130                         135                       140

Ile  Phe  Phe  Ser  Glu  Met  Ile  Lys  Phe  Gln  Leu  Ile  Pro  Ser  Phe  Met
145                       150                     155                       160

Ile  Phe  His  Lys  Ile  Arg  Thr  Leu  Ile  Met  Tyr  Met  Gln  Val  Pro  Asn
                 165                         170                          175

Asn  Val  Glu  Ile  Leu  Thr  Val  Leu  Leu  Glu  His  Ser  Gly  Lys  Phe  Leu
            180                      185                       190

Leu  Asn  Lys  Pro  Glu  Tyr  Lys  Glu  Leu  Met  Glu  Lys  Met  Val  Gln  Leu
       195                      200                      205

Ile  Lys  Asp  Lys  Lys  Asn  Asp  Arg  Gln  Leu  Asn  Met  Asn  Met  Lys  Ser
      210                      215                      220

Ala  Leu  Glu  Asn  Ile  Ile  Thr  Leu  Leu  Tyr  Pro  Pro  Ser  Val  Lys  Ser
225                       230                       235                       240

Leu  Asn  Val  Thr  Val  Lys  Thr  Ile  Thr  Pro  Glu  Gln  Gln  Phe  Tyr  Arg
                 245                        250                        255

Ile  Leu  Ile  Arg  Ser  Glu  Leu  Ser  Ser  Leu  Asp  Phe  Lys  His  Ile  Val
                260                       265                      270

Lys  Leu  Val  Arg  Lys  Ala  His  Trp  Asp  Asp  Val  Ala  Ile  Gln  Lys  Val
            275                      280                       285

Leu  Phe  Ser  Leu  Phe  Ser  Lys  Pro  His  Lys  Ile  Ser  Tyr  Gln  Asn  Ile
       290                      295                        300

Pro  Leu  Leu  Thr  Lys  Val  Leu  Gly  Gly  Leu  Tyr  Ser  Tyr  Arg  Arg  Asp
305                       310                       315                       320

Phe  Val  Ile  Arg  Cys  Ile  Asp  Gln  Val  Leu  Glu  Asn  Ile  Glu  Arg  Gly
                 325                        330                        335

Leu  Glu  Ile  Asn  Asp  Tyr  Gly  Gln  Asn  Met  His  Arg  Ile  Ser  Asn  Val
            340                       345                       350

Arg  Tyr  Leu  Thr  Glu  Ile  Phe  Asn  Phe  Glu  Met  Ile  Lys  Ser  Asp  Val
```

```
                    355                          360                          365
     Leu  Leu  Asp  Thr  Ile  Tyr  His  Ile  Ile  Arg  Phe  Gly  His  Ile  Asn  Asn
          370                      375                      380
     Gln  Pro  Asn  Pro  Phe  Tyr  Leu  Asn  Tyr  Ser  Asp  Pro  Pro  Asp  Asn  Tyr
     385                      390                      395                      400
     Phe  Arg  Ile  Gln  Leu  Val  Thr  Thr  Ile  Leu  Leu  Asn  Ile  Asn  Arg  Thr
                    405                      410                      415
     Pro  Ala  Ala  Phe  Thr  Lys  Lys  Cys  Lys  Leu  Leu  Leu  Arg  Phe  Phe  Glu
                    420                      425                      430
     Tyr  Tyr  Thr  Phe  Ile  Lys  Glu  Gln  Pro  Leu  Pro  Lys  Glu  Thr  Glu  Phe
                    435                      440                      445
     Arg  Val  Ser  Ser  Thr  Phe  Lys  Lys  Tyr  Glu  Asn  Ile  Phe  Gly  Asn  Thr
          450                      455                      460
     Lys  Phe  Glu  Arg  Ser  Glu  Asn  Leu  Val  Glu  Ser  Ala  Ser  Arg  Leu  Glu
     465                      470                      475                      480
     Ser  Leu  Leu  Lys  Ser  Leu  Asn  Ala  Ile  Lys  Ser  Lys  Asp  Asp  Arg  Val
                    485                      490                      495
     Lys  Gly  Ser  Ser  Ala  Ser  Ile  His  Asn  Gly  Lys  Glu  Ser  Ala  Val  Pro
                    500                      505                      510
     Ile  Glu  Ser  Ile  Thr  Glu  Asp  Asp  Glu  Asp  Asp  Asp  Glu  Asn  Asp
                    515                      520                      525
     Asp  Gly  Val  Asp  Leu  Leu  Gly  Glu  Asp  Asp  Ala  Glu  Ile  Ser  Thr
          530                      535                      540
     Pro  Asn  Thr  Glu  Ser  Ala  Pro  Gly  Lys  His  Gln  Ala  Lys  Gln  Asp  Glu
     545                      550                      555                      560
     Ser  Glu  Asp  Glu  Asp  Asp  Glu  Asp  Asp  Glu  Asp  Asp  Asp  Asp  Asp
                         565                      570                      575
     Asp  Asp  Asp  Asp  Asp  Asp  Asp  Gly  Glu  Glu  Gly  Asp  Glu  Asp  Asp  Asp
                    580                      585                      590
     Glu  Asp  Asp  Asp  Asp  Glu  Asp  Asp  Asp  Glu  Glu  Glu  Glu  Asp  Ser
                    595                      600                      605
     Asp  Ser  Asp  Leu  Glu  Tyr  Gly  Gly  Asp  Leu  Asp  Ala  Asp  Arg  Asp  Ile
          610                      615                      620
     Glu  Met  Lys  Arg  Met  Tyr  Glu  Glu  Tyr  Glu  Arg  Lys  Leu  Lys  Asp  Glu
     625                      630                      635                      640
     Glu  Glu  Arg  Lys  Ala  Glu  Glu  Glu  Leu  Glu  Arg  Gln  Phe  Gln  Lys  Met
                    645                      650                      655
     Met  Gln  Glu  Ser  Ile  Asp  Ala  Arg  Lys  Ser  Glu  Lys  Val  Val  Ala  Ser
                    660                      665                      670
     Lys  Ile  Pro  Val  Ile  Ser  Lys  Pro  Val  Ser  Val  Gln  Lys  Pro  Leu  Leu
                    675                      680                      685
     Leu  Lys  Lys  Ser  Glu  Glu  Pro  Ser  Ser  Ser  Lys  Glu  Thr  Tyr  Glu  Glu
          690                      695                      700
     Leu  Ser  Lys  Pro  Lys  Lys  Ile  Ala  Phe  Thr  Phe  Leu  Thr  Lys  Ser  Gly
     705                      710                      715                      720
     Lys  Lys  Thr  Gln  Ser  Arg  Ile  Leu  Gln  Leu  Pro  Thr  Asp  Val  Lys  Phe
                    725                      730                      735
     Val  Ser  Asp  Val  Leu  Glu  Glu  Glu  Lys  Leu  Lys  Thr  Glu  Arg  Asn
                    740                      745                      750
     Lys  Ile  Lys  Lys  Ile  Val  Leu  Lys  Arg  Ser  Phe  Asp
                    755                      760
```

( 2 ) INFORMATION FOR SEQ ID NO:5:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:5:

CCGGAATTCA TGGTCGGTTC CGGTTCT 27

( 2 ) INFORMATION FOR SEQ ID NO:6:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

AGTGACTTGA GCCTC 15